United States Patent [19]

Pini

[11] Patent Number: 5,159,931
[45] Date of Patent: Nov. 3, 1992

[54] APPARATUS FOR OBTAINING A THREE-DIMENSIONAL RECONSTRUCTION OF ANATOMIC STRUCTURES THROUGH THE ACQUISITION OF ECHOGRAPHIC IMAGES

[76] Inventor: Riccardo Pini, 27 Via delle Porte Nuove, I-50144 Firenze FI, Italy

[21] Appl. No.: 438,292

[22] Filed: Nov. 20, 1989

[30] Foreign Application Priority Data

Nov. 25, 1988 [IT] Italy ............................ 09532 A/88

[51] Int. Cl.$^5$ .............................................. A61B 8/00
[52] U.S. Cl. ................... 128/660.07; 128/916; 128/660.1; 73/626
[58] Field of Search .............. 128/916, 660.03, 660.08, 128/660.09, 660.10; 73/625, 626

[56] References Cited

U.S. PATENT DOCUMENTS

| | | | |
|---|---|---|---|
| 4,341,120 | 7/1982 | Anderson | 128/916 X |
| 4,570,488 | 2/1986 | Miwa et al. | 128/916 X |
| 4,771,787 | 9/1988 | Wurster et al. | 128/660.03 |
| 4,846,188 | 7/1989 | Yoshioka | 128/660.05 X |
| 4,967,752 | 11/1990 | Blumenthal et al. | 128/662.06 X |

OTHER PUBLICATIONS

McCann, H. A. et al., "Multidimensional Ultrasonic Imaging for Cardiology", *Proceedings of the IEEE*, vol. 76, No. 9, Sep. 1988, 1063–1073.

Primary Examiner—Francis Jaworski
Attorney, Agent, or Firm—Browdy and Neimark

[57] ABSTRACT

An apparatus that allows the three-dimensional reconstruction of anatomic structures through the acquisition of two-dimensional echographic images produced by the real-time processing of signals reflected and/or scattered by said structures when these are hit by a beam of ultrasound generated, according to a predetermined scanning plane, by a piezoelectric transducer contained within an echographic probe. According to the invention, the scanning plane, in which the sector-scan transducer emits the beam of ultrasound, rotates through an angle of 180°, with intermediate angular increments having a predetermined amplitude and frequency, around the longitudinal axis of the probe, while the latter remains fixed relative to the examined anatomic structure, there being provided means for the actuation and the control of the rotation of the scanning plane. The rotation of the scanning plane with respect to the probe may be obtained either mechanically by means of a motor that rotates the transducer through a predetermined angle, said motor being also arranged to provide the scanning motion to the transducer itself, or electronically by using a transducer constituted by a matrix or array of piezoelectric elements and by selecting a vector of said elements rotating around the longitudinal axis of the probe.

26 Claims, 18 Drawing Sheets

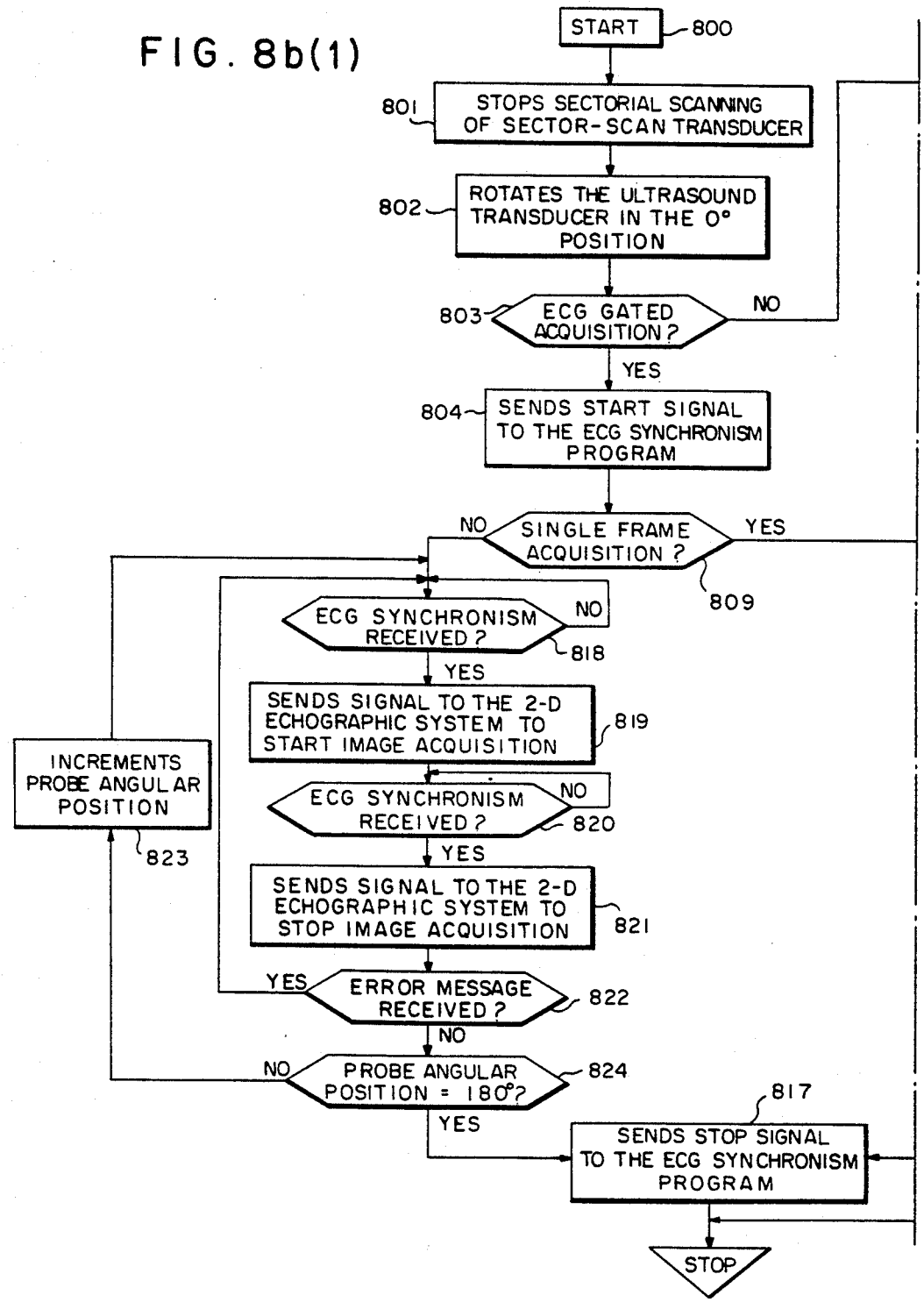
FIG. 8b(1)

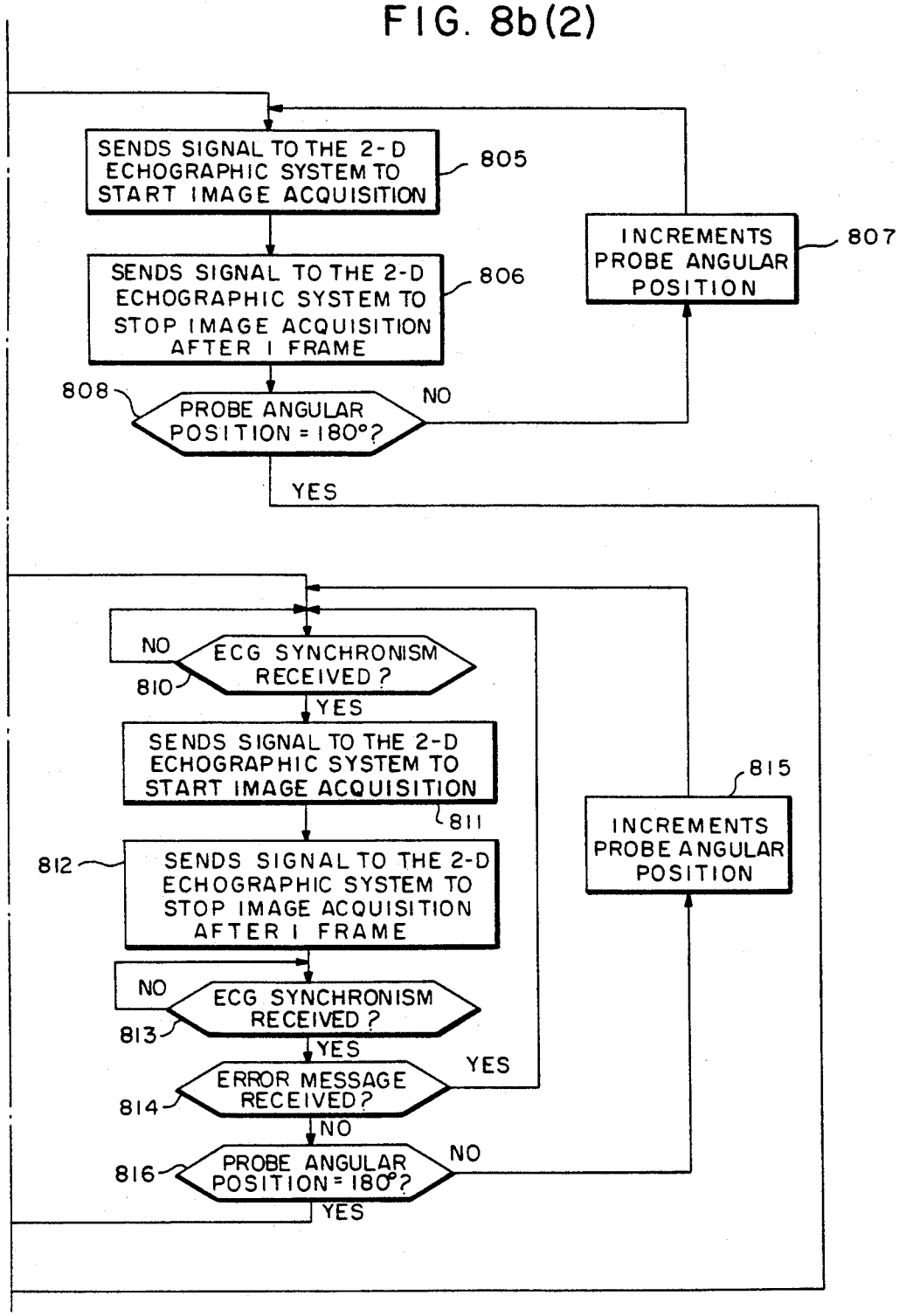
FIG. 8b(2)

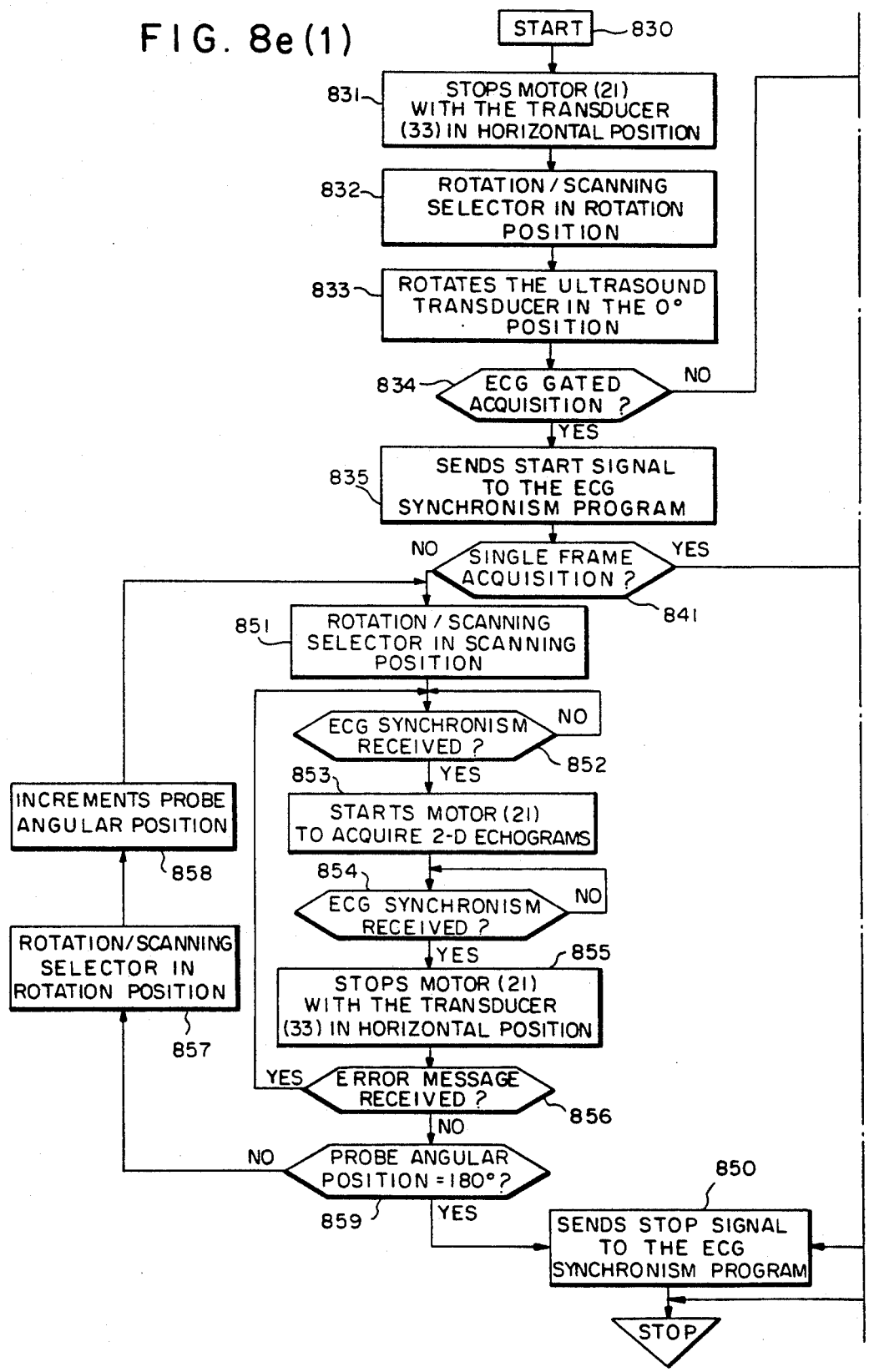

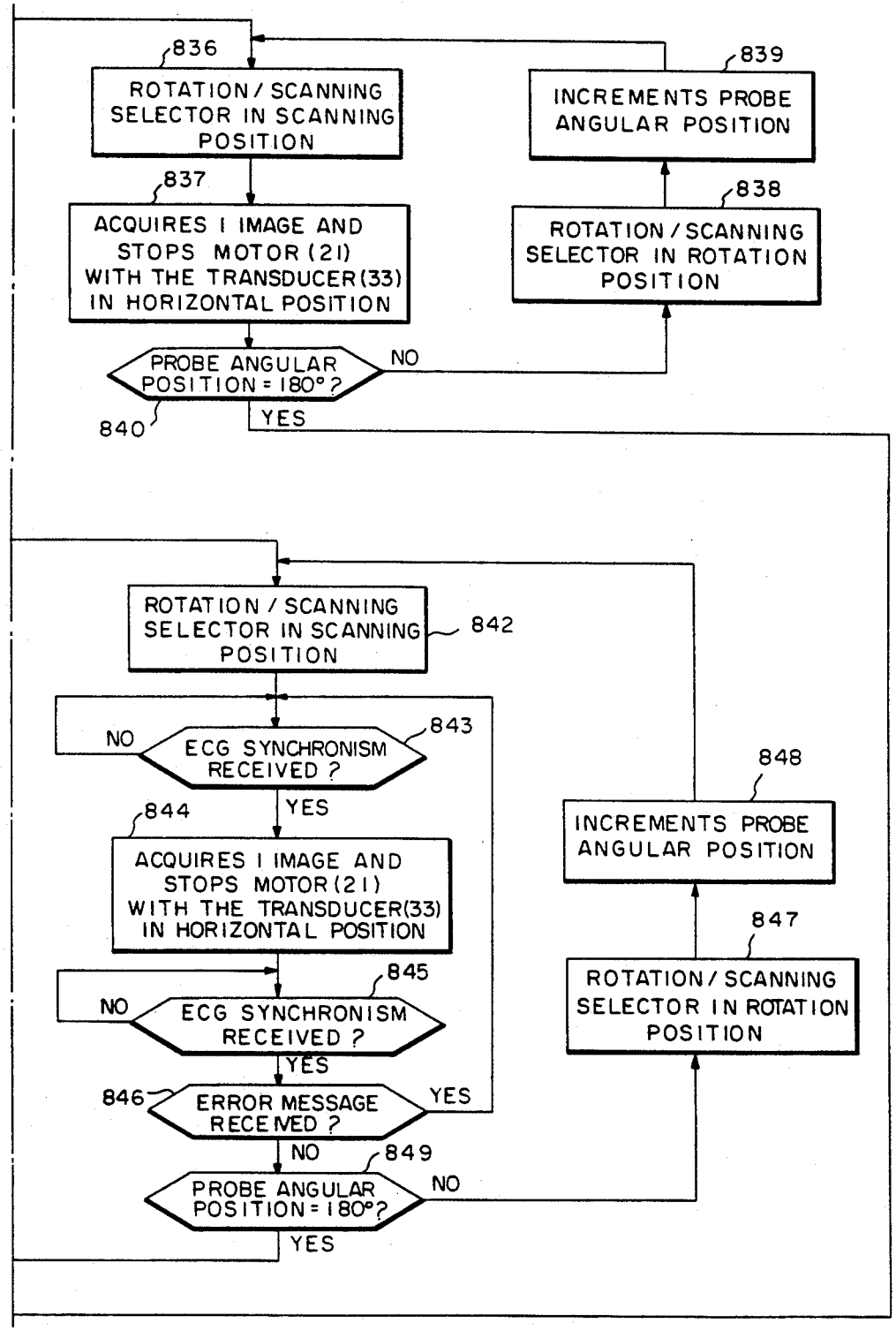
FIG. 8e(2)

APPARATUS FOR OBTAINING A THREE-DIMENSIONAL RECONSTRUCTION OF ANATOMIC STRUCTURES THROUGH THE ACQUISITION OF ECHOGRAPHIC IMAGES

DESCRIPTION

1. Field of the Invention

The present invention relates to an apparatus for the three-dimensional examination of anatomic structures by means of the acquisition of echographic images. More precisely, the invention relates to an apparatus for computerized tomography that allows the three-dimensional reconstruction of anatomic structures by means of the acquisition of echographic images.

More in particular, the object of the present invention is to provide a novel type of probe and apparatus suitable for the acquisition of echographic images which may be utilized for the three-dimensional reconstruction of the anatomic structure being examined.

2. State of the Art

As known, echography is a diagnostic tool which utilizes the properties of ultrasound to penetrate the body of living beings, permitting visualization of the internal anatomic structures (e.g. organs, blood vessels), as well as pathological formations (such as stones or tumors) through the electronic real time processing of the ultrasound waves reflected and/or scattered by the surfaces between tissues having a different acoustical impedance. The echographic examination of a target organ by a transducer of the kind known as "two-dimensional", allows an accurate measurement of the dimensions of the object, an estimate of its shape, and a measurement of its displacements, even if limitedly to a section plane.

A two-dimensional echogram can be obtained with different kinds of scans, but the so-called "sector-scan" echographic transducer is the most popular, at least in cardiology, because it functions also when only limited acoustic "windows" are available. To realize the selection of the several lines of sight that constitute the two-dimensional image, both mechanical and electronic means have been used. With the mechanical sector-scan transducers several lines of sight are selected by means of an electric motor which, shifting the piezoelectric ceramic, controls the orientation of the ultrasound beam. On the contrary, the electronic sector-scan transducers use an array of piezoelectric elements, and the ultrasound beam is orientated by adjusting the firing sequence of the several elements using the "phased array" principle. In other words, by firing simultaneously all of the piezoelectric array elements, the ultrasound beam is emitted perpendicularly to the transducer, because the wavefront resulting from the addition of the single components remains parallel to the surface of the transducer. If, on the contrary, the elements are fired with increasing delays, by adjusting both the magnitude and the direction of the delay, the direction of the ultrasound beam can be controlled. Thus, both mechanical and electronic sector-scan transducers allow the visualization of a single flat section of the examined organ, and consequently the operator must shift the probe in order to obtain sections with different spatial orientations from which to derive in his mind a three-dimensional representation as accurate as possible.

The physical characteristics of ultrasound and the anatomical location of certain organs limit the realization of an apparatus for ultrasound tomography using the same technique utilized for X-ray or nuclear magnetic resonance computerized tomography. In fact, ultrasound propagates in air with an extremely great attenuation, and for this reason there must be a good coupling between the transducer and the body surface to which it is applied, interposing therebetween either a layer of a material having an acoustic impedance with a value near to that of biological tissues, or for particular structures such as breasts or limbs, immersing the examined parts in a water tank. Therefore, organs surrounded by anatomical structures containing air, such as the heart, can be examined only through a limited number of acoustic windows, which correspond to areas in which the gas filled lungs are not interposed between the surface of the rib cage and the heart; through such windows two-dimensional images are obtained which are orientated along the major or minor axis of the left ventricle trying to examine as many areas as possible in order to get a more complete evaluation of the anatomy and function of the heart.

Consequently, methods and apparatus have been devised for the ultrasound three-dimensional reconstruction of anatomic structures which take into account the unique characteristics of the echographic technique. These methods and apparatus are based on the acquisition of two-dimensional images with a known spatial orientation with respect to an external reference system, the manual identification of the contours on each image, and then the reconstruction of a three-dimensional model by contour interpolation.

Two methods have been initially proposed for detecting the exact position of the two-dimensional images. According to one method the echographic probe is connected to a mechanical arm provided with suitable sensors which continuously record the transducer orientation. According to the other method, multiple spark gaps are affixed to the outer envelope of the echographic probe, while in the room destined to perform the echographic examination, three microphones are located, arranged at right angles each with respect to the other, by means of which it is possible to calculate by triangulation the transducer position. Both these methods, however, have little clinical application, because the mechanical arm makes the operation of transducer positioning very difficult, while the acoustic system limits appreciably the portability of the echographic apparatus, a key feature of such diagnostic procedure. Further, these methods also have the disadvantage of giving no information about changes in the position of the subject being examined, and, consequently, if the patient moves during the examination, the reconstruction data can be affected by errors without possibility of control by the operator. Finally, the three-dimensional reconstruction with these systems requires the contour identification in all the acquired images with the double inconvenience of the loss of a certain amount of anatomic information (structures such as the heart have such irregular internal contours that it is practically impossible to track them accurately) and the consequent reconstruction of a schematic model which a physician can interpret only with difficulty.

The purposes of the present invention are as follows:

to provide an apparatus for performing ultrasound computerized tomography of anatomic structures which is not bound to an external reference system for the spatial localization of the numerous two-dimensional images necessary for the three-dimensional reconstruction of said anatomic structure;

to provide an apparatus of the above-mentioned kind capable of producing a non-schematic three-dimensional representation of the examined structures, with a good spatial and time resolution as the standard two-dimensional echographic technique;

to provide an apparatus of the above mentioned kind that is structurally simple, easy to use and of low cost.

The main characteristic of the apparatus according to the invention resides in the fact that the reference frame necessary for the spatial localization of the several two-dimensional images of the anatomic images to be examined is defined by the echographic probe itself, which is maintained fixed with respect to said structure, while the ultrasound transducer, the driving of which causes the emission of the ultrasound beam, rotates around the longitudinal axis of the probe itself. Thus, for each two-dimensional image of the examined anatomic structure, corresponds a well defined angular displacement of the scanning plane with respect to a reference position. Since the rotation axis of the transducer coincides with the axis of symmetry of the scanning plane along which the several two-dimensional images are obtained, a 180° rotation of the transducer is sufficient to cover all the 360° that are required for the three-dimensional reconstruction of the structure. Moreover, comparing the first (0° of rotation) and the last (180° of rotation) image, provides an immediate and accurate check of the stability of the probe with respect to the examined anatomic structure: indeed, if the probe and the target anatomic structure maintain the same relative position during the entire acquisition, the two images will be mirror images.

Based on a further characteristic of the apparatus according to the present invention, the rotation of the ultrasound transducer around the longitudinal axis of the probe may be obtained mechanically or electronically. With the former technical solution, an electric motor, such as a stepper motor, rotates the transducer according to subsequent scanning planes spaced from one another with a predetermined angular increment. With the electronic solution, the rotation of the scanning plane is obtained using a matrix, or multiple arrays, of piezoelectric elements on which to select electronically the vector of elements corresponding to the desired angular rotation; one of the vectors constitutes the reference plane for all the subsequent three-dimensional reconstructions.

SUMMARY OF THE INVENTION

The present invention is an apparatus for obtaining the three-dimensional reconstruction of anatomic structures by means of the acquisition of two-dimensional echographic images obtained by the real time processing of reflected and/or scattered signals from said structures when they are hit by an ultrasound beam produced, along a predetermined scanning plane, by a piezoelectric ceramic of an echographic probe, said probe being associated to means for scan control and for the processing of the received ultrasound signals and the display of the image reconstructed from said signals, said apparatus being characterized in that the scanning plane, along which said piezoelectric ceramic emits said ultrasound beam, rotates through a 180 angle with intermediate angular increments having a predetermined magnitude and frequency around the longitudinal axis of the probe while this latter stays fixed relative to the examined anatomic structure, means being provided for the actuation and the control of the rotation of said scanning plane.

BRIEF DESCRIPTION OF THE DRAWINGS

Further features and advantages of the apparatus for the three-dimensional examination of anatomic structures through the acquisition of echographic images will result more clearly from the following disclosure of embodiment thereof, given by way of non limitative example, and with reference to the attached drawings, wherein:

FIG. 8b shows a flow-chart of the program for acquiring a complete series of echographic images with the apparatus according to the present invention, provided with a first kind of echographic sector-scan probe, of a mechanical type;

FIG. 8e shows a flow-chart of the program for acquiring a complete series of echographic images with the apparatus according to the present invention, provided with a second kind of echographic sector-scan probe, of a mechanical type;

DESCRIPTION OF THE PREFERRED EMBODIMENTS

Figure 1:
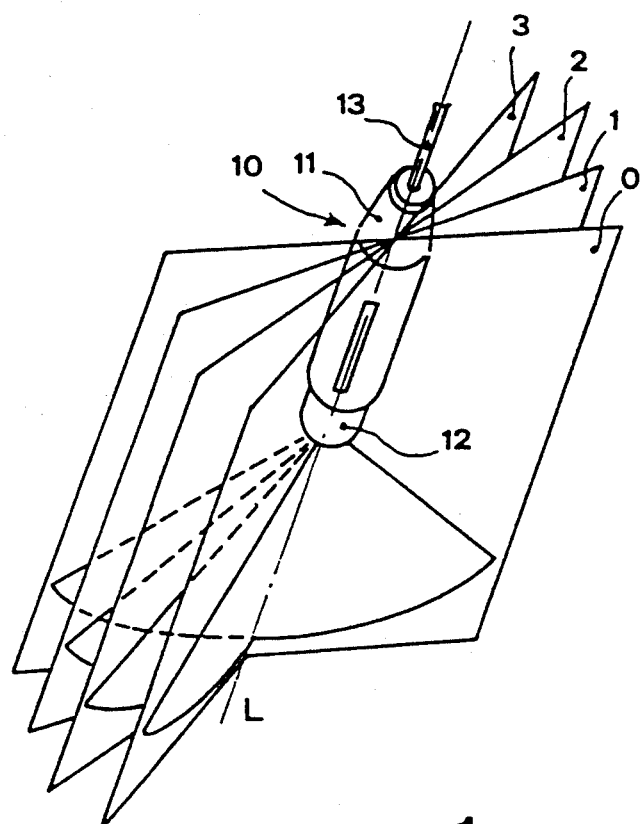
FIG. 1 shows schematically an echographic sector-scan probe according to the present invention.

In FIG. 1, a sector-scan echographic probe according to the present invention is schematically represented as 10; this probe comprises an outer tubular housing 11 from an end of which an ultrasound transducer 12 protrudes. The transducer 12 emits a sectorial beam of ultrasound in a conventional manner and it is electrically connected to means for its operation, not shown, through the cable 13. According to the invention the ultrasound transducer 12 is rotated around the longitudinal axis L of the probe to collect two-dimensional images in different scanning planes with predetermined angular increments, four of which are shown by way of example in FIG. 1 and identified as 0, 1, 2, 3. With this transducer a series of two-dimensional images is acquired, with a constant angular increment up to covering a rotation of 180°. Since the rotation axis coincides with the symmetry axis of the two-dimensional sector, a rotation of 180° is sufficient to cover all of the 360° necessary for the three-dimensional reconstruction. In order to obtain an accurate three-dimensional reconstruction of the anatomic structures, the angular increment should be smaller than the lateral resolution of the ultrasound transducer; thus the total number of the two-dimensional images which are necessary for the reconstruction of the three-dimensional model is 180° divided by the angular increment.

Figure 2:
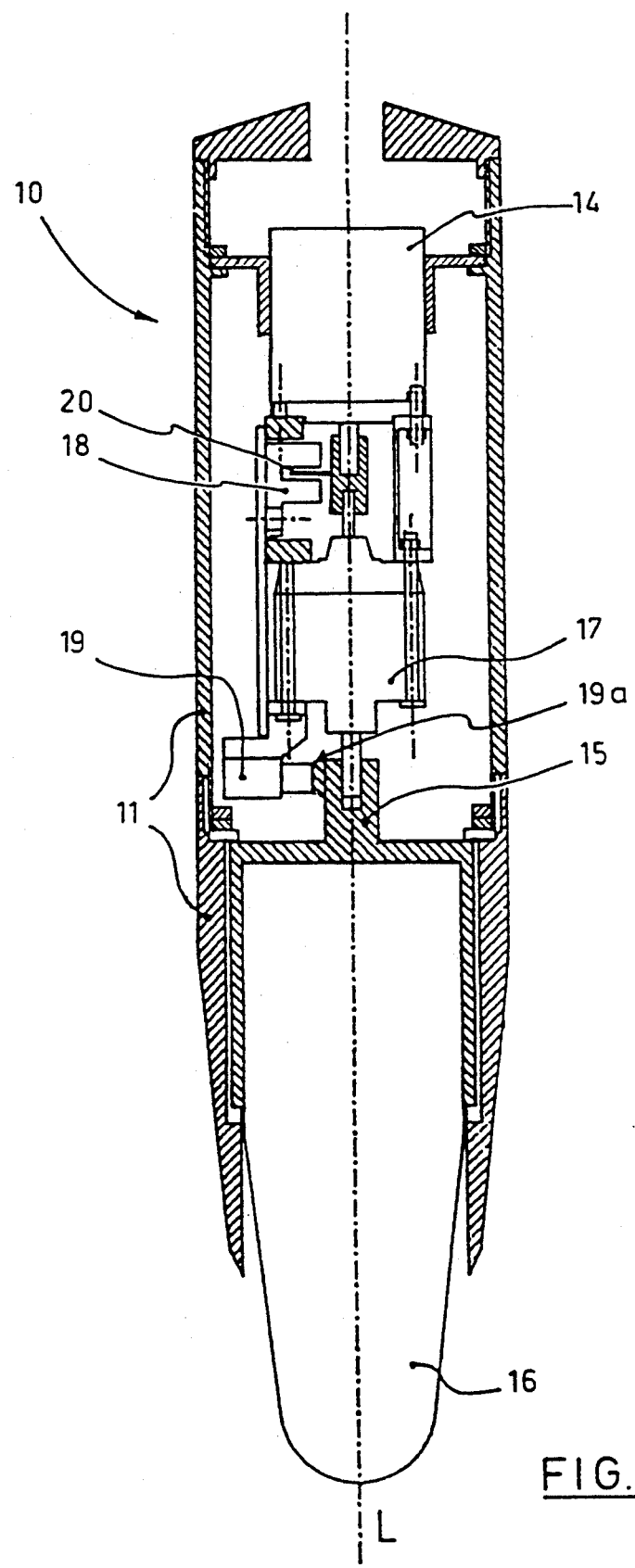
FIG. 2 is a schematical view in longitudinal section of an echographic sector-scan probe, of a mechanical type, according to the present invention.

With both mechanical and phased array sector-scan transducers, the rotation of the assembly carrying the ultrasound transducer 12 may be obtained by means of an electric motor interposed between the support assembly of the transducer itself and the fixed part 11 of the probe 10. As shown in FIG. 2, a first example of a sector-scan probe according to the invention may then be realized with a fixed tubular part 11 housing an electric motor 14 rigidly fastened thereto, and a support 15 for an ultrasound transducer 16 rotatably mounted within the fixed part 11 and connected to the motor 14 to be rotated by it.

A step-down gearbox 17 which reduces the number of revolutions of the motor 14 by 120 times is interposed between the motor 14 and the support 15; consequently to each full revolution of the motor 14 corresponds an angular increment of 3° of the probe 16. The selection of the step-down ratio of 120:1 is a consequence both of the lateral resolution of the transducer used in this construction and of the output power of the motor 14. The probe 10 is provided with a switch 19 which, actuated by a cam 19a located on the shaft of the support 15, detects the mechanical-zero position of the same. The probe 10 is also provided with an optical gate 18 of a known type which, in cooperation with a tab 20 fastened to the shaft of the motor 14, allows the control of the number of angular increments to which the transducer 16 is subjected.

This kind of probe may use either a phased array transducer or a mechanical transducer; in the latter case the transducer is provided with its own motor, as is well known, for permitting the sectorial scanning.

In another probe according to the invention which makes use of a mechanical sector-scan transducer, an electric motor which allows both the sectorial scanning of the transducer and the rotation of the same around the longitudinal axis of the probe can be used. This embodiment of the present invention is shown in detail in FIG. 3.

In this figure, the outer shell of the end of the probe 10—which envelops the piezoelectric ceramic, the motor, and the several moving components—is indicated as 20. In the interior of the probe 10 is mounted a stepper motor 21, or an equivalent one, connected to an annular support 22 fastened to the interior of the shell 20 of the probe 10 and provided centrally with a tubular extension 22a; within this tubular extension 22a, a wall 23 is fastened that is traversed by the motor shaft 24. Moreover, the plate 22 supports rotatably in positions diametrically opposed with respect to the shaft 24, a pair of uprights 25a and 25b, by a ball bearing 26 having its inner ring fastened to the tubular extension 22a of the plate 22. On the free end of the shaft 24 there is force fitted a bevel gear 27 meshing with a sector bevel gear 28 fastened on a transversal shaft 31 parallel to the pin 29 supported by ball bearings 32 located at the end of the uprights 25a and 25b. The sector bevel gear 28 is, in its turn, rotatably mounted on a pin 29 at right angles with the shaft 24, fastened to the upright 25a. The shaft 31 is connected in a known way to the block 33 of piezoelectric elements which emit the ultrasound beam, an assembly that, owing to the above described mechanical interconnections, is provided with a reciprocating oscillatory motion with respect to the axis 7 of the shaft 31. At the center of the plate 23 is fastened a sleeve, coaxial with respect to the shaft 24, having an internal edge 34a whereon a helical spring 35 rests, pushing on a collar 36 slidably mounted on the shaft 24. Between the tubular extension 22a and the sleeve 34 is located an annular electromagnet 37 fastened to the plate 23, while a disk 38 is fastened to the collar 36; the disk 38 is provided with two diametrical seats 39 suitable to be engaged by two corresponding teeth 40 protruding from a body 41 integral with the toothed gear 27 and consequently with the shaft 24. The disk 38 is moreover slidably engaged with two pins 42 extending from the uprights 25a and 25b so that said disk is firmly connected with said uprights.

The stepper motor 21 gives to the shaft 24 a reciprocating angular motion that, in the scanning phase, is transmitted to the group of piezoelectric elements 33, while the electromagnet 37 is energized, thus preventing the transmission of the motion also to the two uprights 25a and 25b, because the disk 38, attracted by the electromagnet 37, is disengaged from the body 41. On the contrary, when the scanning plane has to be changed, the stepper motor is stopped in the intermediate position, i.e. the position in which the group 33 is in the horizontal position, the electromagnet 37 is deenergized, and consequently the disk 38, pushed by the spring 35, engages the body 41. In this way, by driving the motor 21 again, the two uprights 25a and 25b, fastened to the disk 38 by means of the pins 42, are rotated through a predetermined angle and with them the whole group of the piezoelectric elements 33. The subsequent energization of the electromagnet 37 presets the probe for the scanning phase along a new scanning plane that is rotated with respect to the former one.

Figure 4:
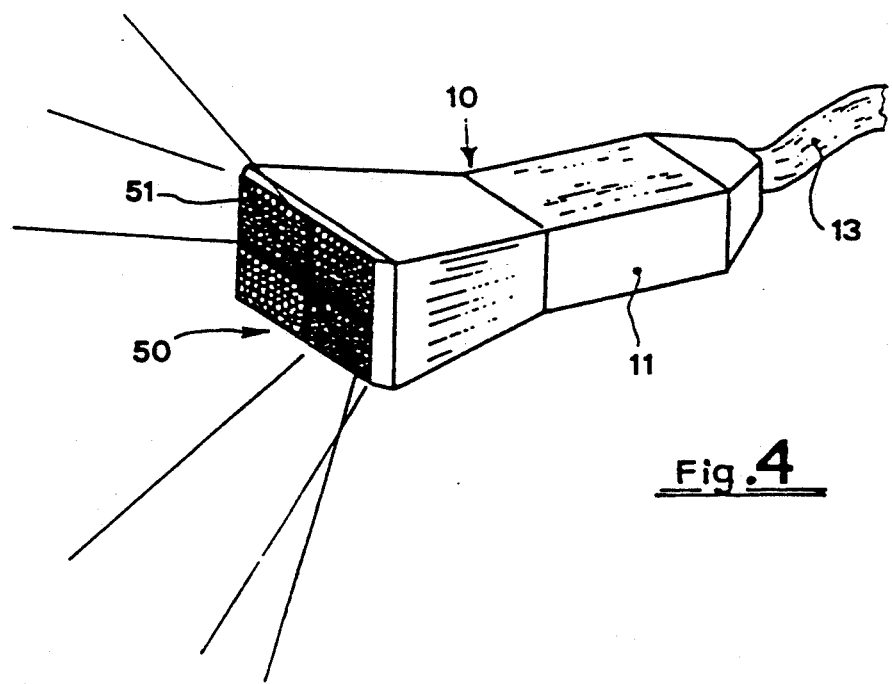
FIG. 4 shows in schematical perspective view an echographic sector-scan probe, of an electronic type, according to the present invention.

According to another embodiment of the invention, in FIG. 4, an electronic sector-scan probe 10 is schematically represented with the transducer 50, constituted of a matrix of piezoelectric elements; on this matrix a vector 51 of elements that identifies the scanning plane can be selected electronically.

To each vector of piezoelectric element a scanning plane will univocally correspond, while one of the vectors will be selected as a reference for the identification of the relative position of the several scanning planes.

In sector-scan probes of the electronic kind, the transducer may also be realized by means of arrays of piezoelectric elements, constituted of at least two arrays crossing each other at the center of the transducer. The selection of the scanning planes passing through the center is obtained by firing the single elements of each array with variable delays, as it is usually done in the conventional electronic transducers.

For the drive of the transducer an electronic system is provided for the serial acquisition of the echographic images by either controlling the motion of the motor which rotates the transducer or selecting the correct vector of the ceramic elements of the matrix; the same electronic system also allows the acquisition of orthogonal two-dimensional images that are necessary for the standard two-dimensional echographic examination, thus avoiding the manual rotation of the probe.

For a probe like the one shown in FIG. 2 in which a motor 14 rotates the sector-scan transducer 16 around the longitudinal axis L of the probe 10, the apparatus (refer to FIG. 5) comprises means for the two-dimensional scanning, which control the sectorial scanning motor.

The apparatus, moreover, includes an electronic circuit dedicated to the rotation of the transducer 16. This circuit, indicated as transducer rotation adapter, feeds the motor 14 dedicated to the rotation, while a control circuit, associated to a rotation sensor constituted by an optical gate 18 and a tab 20 fastened to the shaft of the motor 14, allows the clockwise or counterclockwise rotation of the transducer by the corresponding switches.

Figure 5:
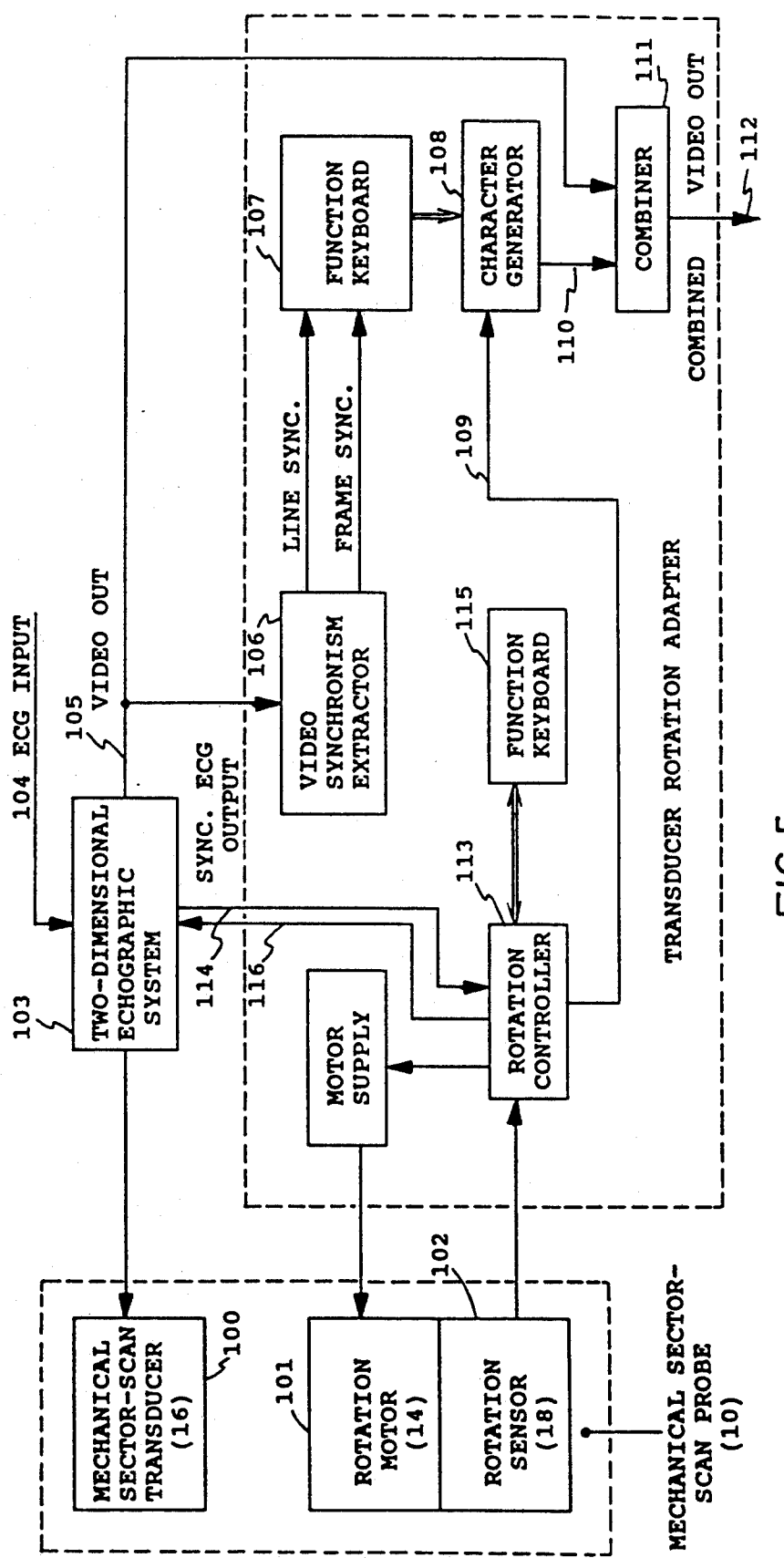
FIG. 5 shows a block diagram of the control circuitry of the apparatus according to the present invention provided with a first kind of echographic sector-scan probe, of a mechanical type.
Figure 6:
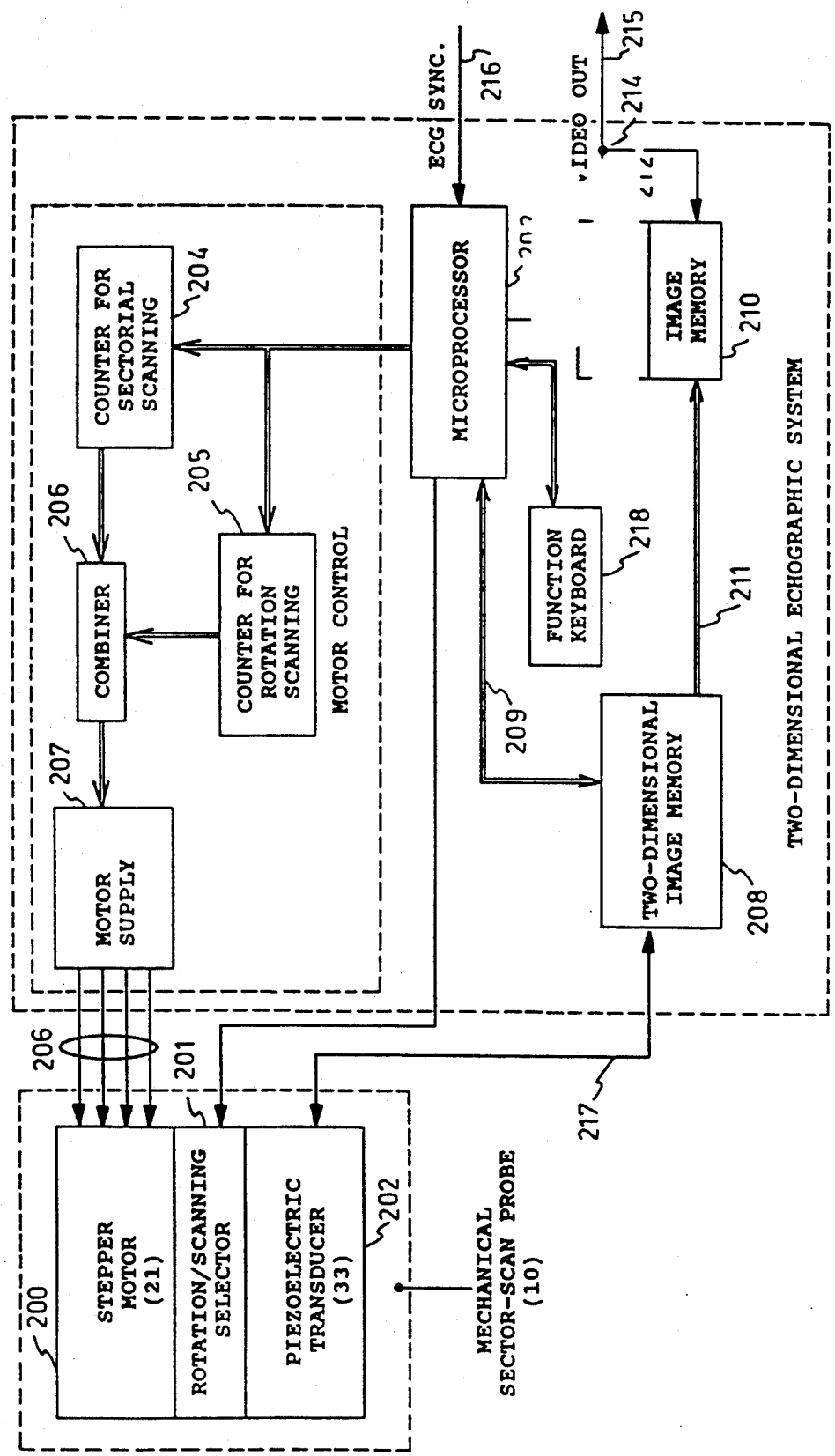
FIG. 6 shows a block diagram of the control circuitry of the apparatus according to the present invention, provided with a second kind of echographic sector-scan probe, of a mechanical type.

Reference will now be made to FIGS. 5 and 6 relating to circuitries for the control of the echographic probes shown in FIGS. 2 and 3, respectively.

Referring to FIG. 5 the block diagram therein shown includes a block 10 indicating generally an echographic probe 10 like the one shown in FIG. 2. The probe 10 is represented divided into three blocks respectively indicated as 100, corresponding to a mechanical sector-scan transducer; 101, corresponding to the electric motor 14 for the transducer rotation; and 102 corresponding to the optical gate 18. The transducer contained in the block 100 is controlled by a two-dimensional echographic system of a state-of-the-art type schematically shown as 103. The system 103 is provided with an input 104 for an electrocardiographic (ECG) signal for synchronizing its operation with the heart-beat of a patient, as will be described hereinafter in greater detail. The system 103 is provided with a video output 105 constituted by a conventional composite video signal containing video information, line synchronizing pulses and frame/field synchronizing pulses. The video signal present on the output 105 is applied to a conventional synchronism separator circuit 106 from which line synchronism signals and frame synchronism signals are obtained, which are applied to a group of counters, represented with block 107, for controlling a character generator 108. The character generator 108 is also supplied with a signal on line 109 coming from the transducer rotation controller, as will be seen below. The output 110 of the character generator 108 is applied to a first input combiner circuit 111, the other input of which is supplied with the composite video signal available on the output 105 of block 103. The output 112 of the combiner circuit 111 is constituted by frames of pictures of two-dimensional scanning "labelled" with information about their angular location with reference to a predetermined "zero position" derived from the echographic probe itself.

As mentioned above, the transducer angular position is sent to the character generator 108 from block 113 which controls the rotation of the motor 14 contained within the echographic probe through line 109. Block 113 is associated to the function keyboard 115 that controls the acquisition modalities. In fact, through this keyboard, the user can select the acquisition of a single frame in each cardiac cycle or the acquisition of the entire cardiac cycle. In the former situation, the user must select a time-delay by a digital switch in order to start the echographic acquisition at different times from the onset of the QRS wave. Moreover, the keyboard has a switch to inform the rotation controller if a patient is in atrial fibrillation because in this pathological condition it is impossible to recognize the extrasystolic beats comparing the cardiac cycle duration. The block 113 also controls the rotation speed and direction of the motor 14 by its power supply.

Block 113 is also fed with an ECG synchronism signal 114 derived from the system 103 when it is necessary to execute the echographic scans in synchronism with the heart-beat.

The rotation controller 113 sends a synchronism signal through line 116 to the two-dimensional echographic system 103 to start the sectorial scanning of transducer 16 in synchronism with the ECG signal, if necessary for the three-dimensional reconstruction. The selection of an ECG gated acquisition is performed by operating a switch on the keyboard 115.

Figure 3:
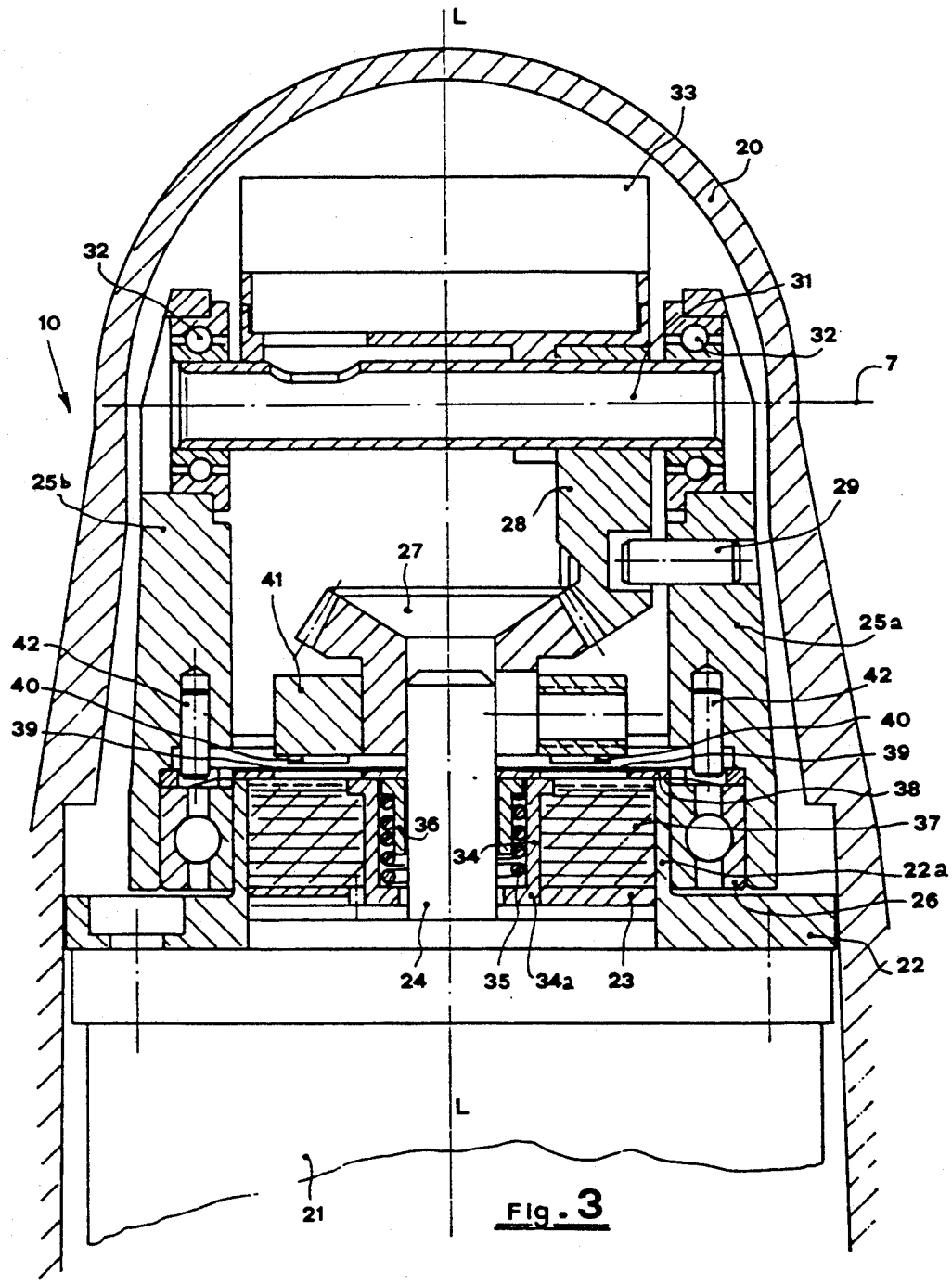
FIG. 3 is a partial longitudinal sectional view of an echographic sector-scan probe, of a mechanical type, according to the present invention.

FIG. 6, which relates to a control circuitry for an echographic probe as shown in FIG. 3, will now be explained.

The circuitry of FIG. 6 is arranged to cooperate with an echographic probe comprising a stepper motor 21, indicated as block 200, a selector of scanning/rotation planes represented by block 201 electrically constituted by an electromagnet (see FIG. 3) and a block 202 representing the piezoelectric transducer 33. The circuitry of FIG. 6 is centered on a microprocessor indicated as a whole with block 203. The microprocessor 203 controls a counter for the sectorial scanning, indicated as block 204, and a counter for the rotation control, indicated as block 205. The outputs of counters 204 and 205 are combined together in the combining block 206 for controlling a stepper motor driver, indicated as block 207. The four-phase power signals 206 which command the stepping motor contained in block 200 output from block 207.

The piezoelectric transducer contained in block 202 is connected through a bidirectional line 217 to a two-dimensional image generator 208, which is also connected to the microprocessor 203 through a bus 209, and to an image memory unit 210 through a bus 211. Memory 210 is associated to a further graphic memory 212, controlled with a line 213 by the microprocessor 203, for the "labelling" of the images stored in the memory 210 in a manner similar to that described with reference to FIG. 5. The outputs of the memories 210, 212 are combined at the node 214 to provide a combined video signal output 215 as disclosed with reference to FIG. 5.

Similarly to the circuit of FIG. 5, microprocessor 203 is provided with an input for an electrocardiographic synchronism signal 216 for use when it is necessary to synchronize the scans with the heart-beat and it is connected to a function keyboard 218 to select the acquisition modalities.

Figure 7:
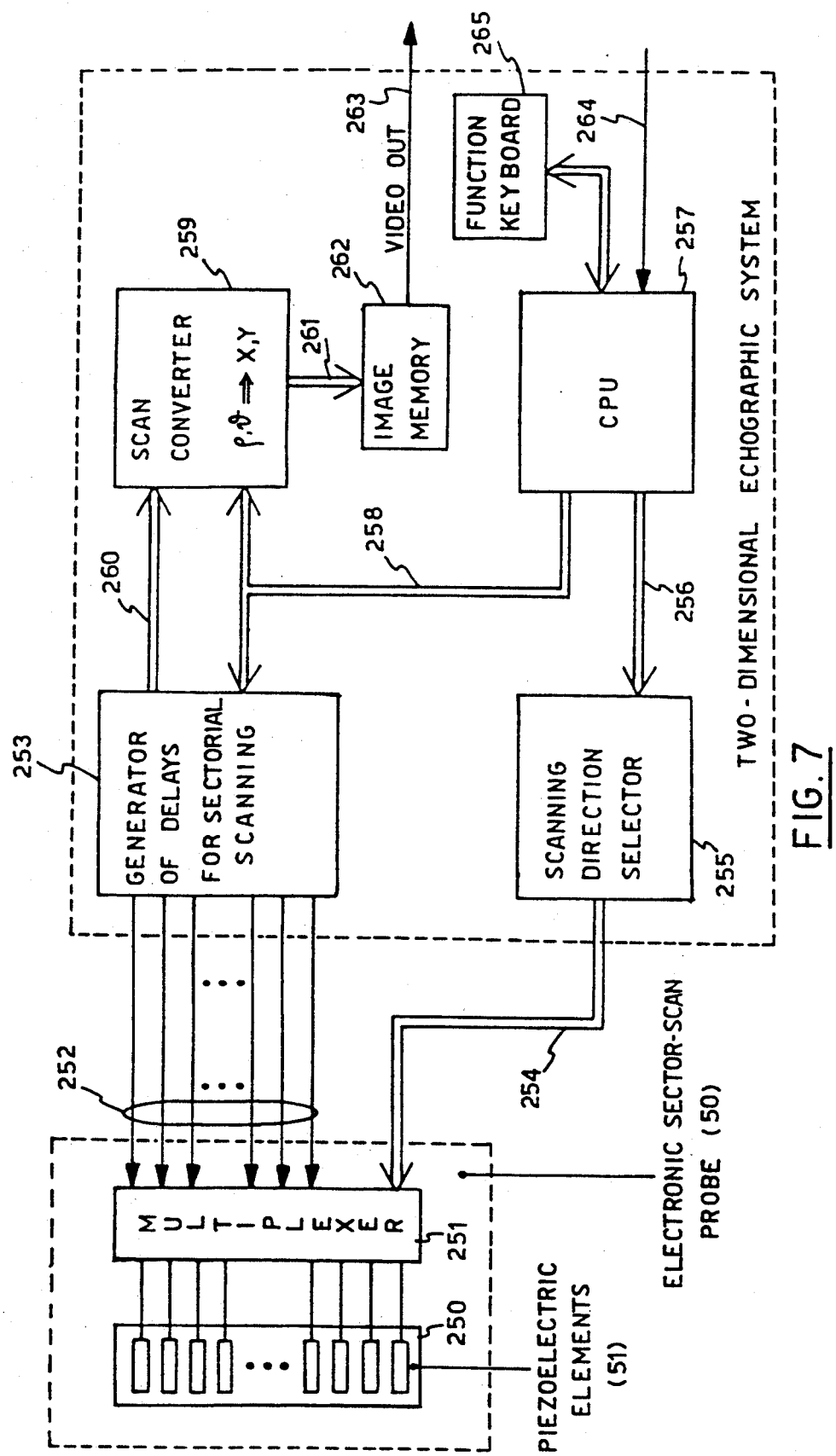
FIG. 7 shows a block diagram of the control circuitry of the apparatus according to the invention, provided with an echographic sector-scan probe, of an electronic type.

With reference to FIG. 7, the control circuit for the echographic probe of FIG. 4 will now be disclosed.

The circuitry of FIG. 7 is arranged to cooperate with an echographic probe comprising an array of piezoelectric elements 51 (block 250), driven by a multiplexer 251 fed on one hand through a bundle 252 of coaxial cables by a transmit/receive generator of the delay for the sectorial scanning shown in 253.

The multiplexer 251 is also driven through a bus 254 by a selector of the scanning direction shown in block 255 and controlled through a bus 256 by a CPU 257. The CPU 257 also controls, through a further bus 258, both said delay generator 253 and a polar-to-rectangular scan converter 259. The latter is also fed with echo data from block 253 by means of a bus 260. The scan converter 259 is connected with a bus 261 to an image memory 262 from which serial video signals are outputted over line 263.

As in the embodiments of FIGS. 5 and 6 a line 264 brings to the CPU 257 a signal for the synchronization with the ECG signal and a function keyboard 265 allows the selection of different acquisition modalities.

Figure 8:
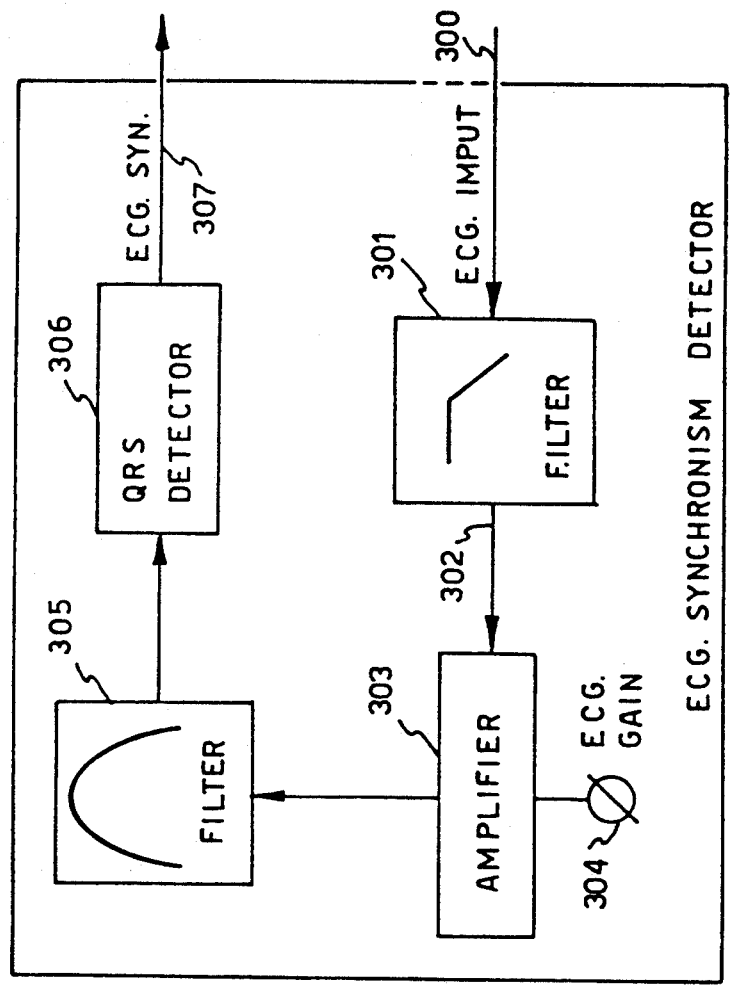
FIG. 8 shows a block diagram for an auxiliary circuit for synchronizing the apparatus according to the invention with the heart-beat of a patient.

Reference is now made to FIG. 8, which shows a circuit for deriving the synchronism signals from the ECG signals. The ECG signal is applied on input terminal 300, from which it is applied to a first filter unit 301 for suppressing unwanted high-frequency noise components. The output of the filter 301 is applied to the input 302 of a variable gain amplifier 303 whose gain may be adjusted by means of a control 304. The output of the amplifier 303 is applied to a filter 305 of the bandpass type, arranged for enhancing the pulse component of the QRS wave. The output of the filter 305 is then applied to a QRS detector 306 comprising, in a known way, a threshold detector and a waveshaper, for providing on the output 307 a signal suitable for synchronizing the operation of the ultrasonic echographic scanner as above described.

The ECG synchronism is processed in accord with the function keyboard setting prearranged by the user as described below.

Figure 8A:
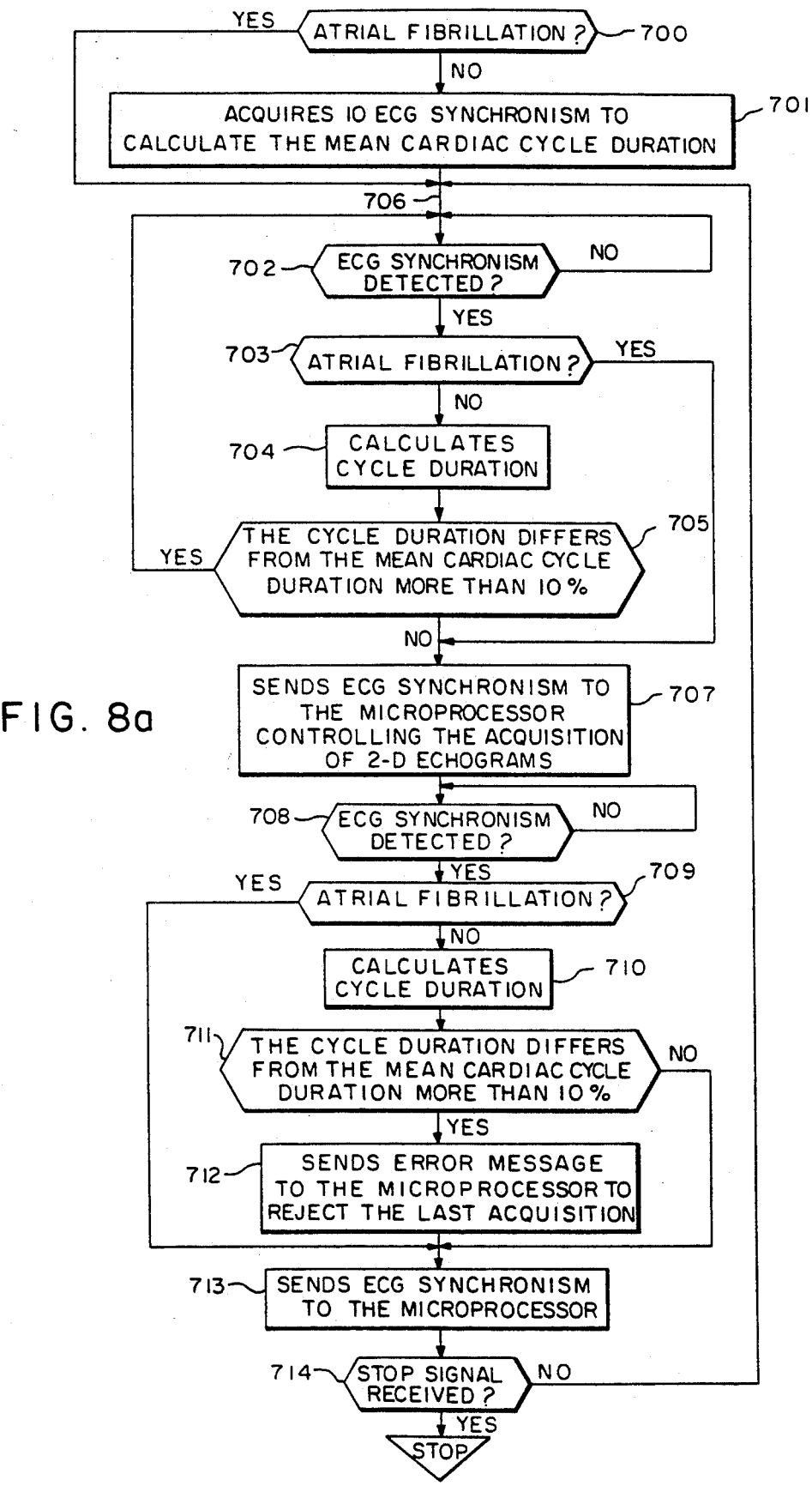
FIG. 8a shows a flow-chart of the program for synchronizing the apparatus according to the invention with the heart-beats of a patient.

Reference is now made to FIG. 8a showing the processing arrangement of the ECG synchronism signals to reconstruct the three-dimensional model of the heart in a specified moment of the cardiac cycle. The execution of the program shown in the flow-chart of FIG. 8a is started by the program controlling the acquisition of the two-dimensional images when the operator selects the ECG-gated modality and he presses the START key on the function keyboard. As first step, the program checks if the user pushed the function keyboard key to indicate the presence of atrial fibrillation (box 700); if the key is not depressed, the program calculates the mean cardiac cycle duration on 10 consecutive beats (box 701) to obtain a reference value to identify the presence of arrhythmias during the acquisition process. In the presence of atrial fibrillation—indicated by a depressed key in the function keyboard—the program does not calculate the mean cardiac cycle duration because, in this pathological condition, it is impossible to identify extrasystolic beats by comparing the cardiac cycle duration. After this first step, the program waits (box 702) until it receives an ECG synchronism signal from the circuit described in FIG. 8 and, if atrial fibrillation is not present (box 703), it calculates the cardiac cycle duration (box 704) to check for arrhythmias (box 705). A heart beat is defined arrhythmic if the cycle duration differs more than 10% from the mean cardiac cycle duration. In the presence of an extrasystole, the program rejects the postextrasystolic cycle coming back to the connection point 706. If the heart beat is rhythmic, the program sends the ECG synchronism to the microprocessor controlling the acquisition of the two-dimensional echograms (box 707). The microprocessor processes the ECG synchronism signals differently in accordance with the different systems presented in FIGS. 5, 6 and 7; moreover, the process differs if the user selected the acquisition of a single frame or of an entire cardiac cycle. When the next ECG synchronism is detected (box 708), if the atrial fibrillation is absent (box 709), the program calculates the cardiac cycle duration (box 710); then, if the rhythm is irregular (box 711), it sends an error message to the microprocessor to reject the last acquisition (box 712). In any case, the program sends a synchronism signal to the microprocessor to indicate the cardiac cycle end (box 713). The program step, starting from the connection point 706, is repeated until the program receives a stop signal (box 714) from the microprocessor controlling the acquisition as described below.

Figure 8C:
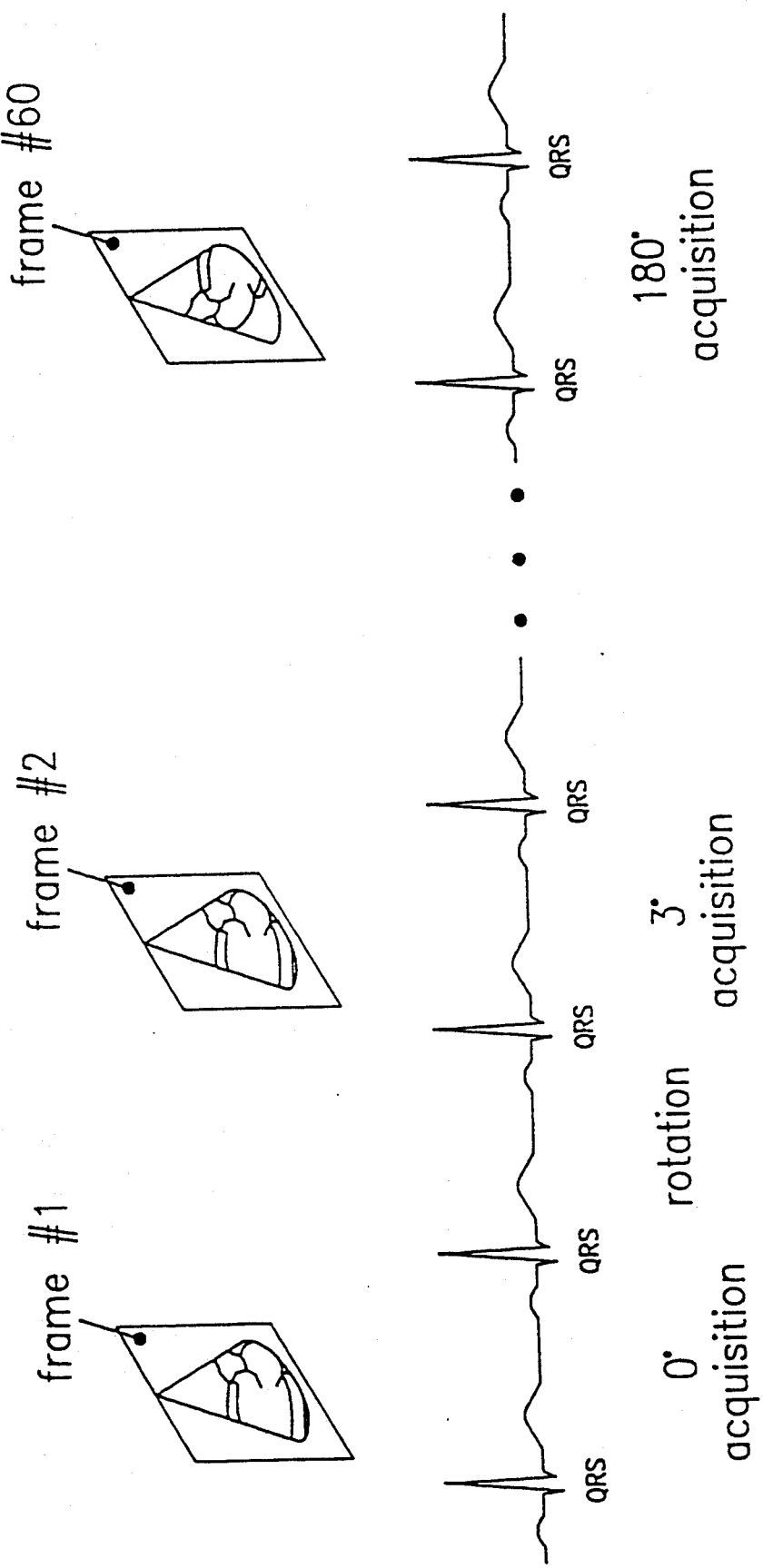
FIG. 8c shows a schematic representation of the acquisition process for the three-dimensional reconstruction of the heart in a specified moment of the cardiac cycle with the apparatus according to the present invention.
Figure 8D:
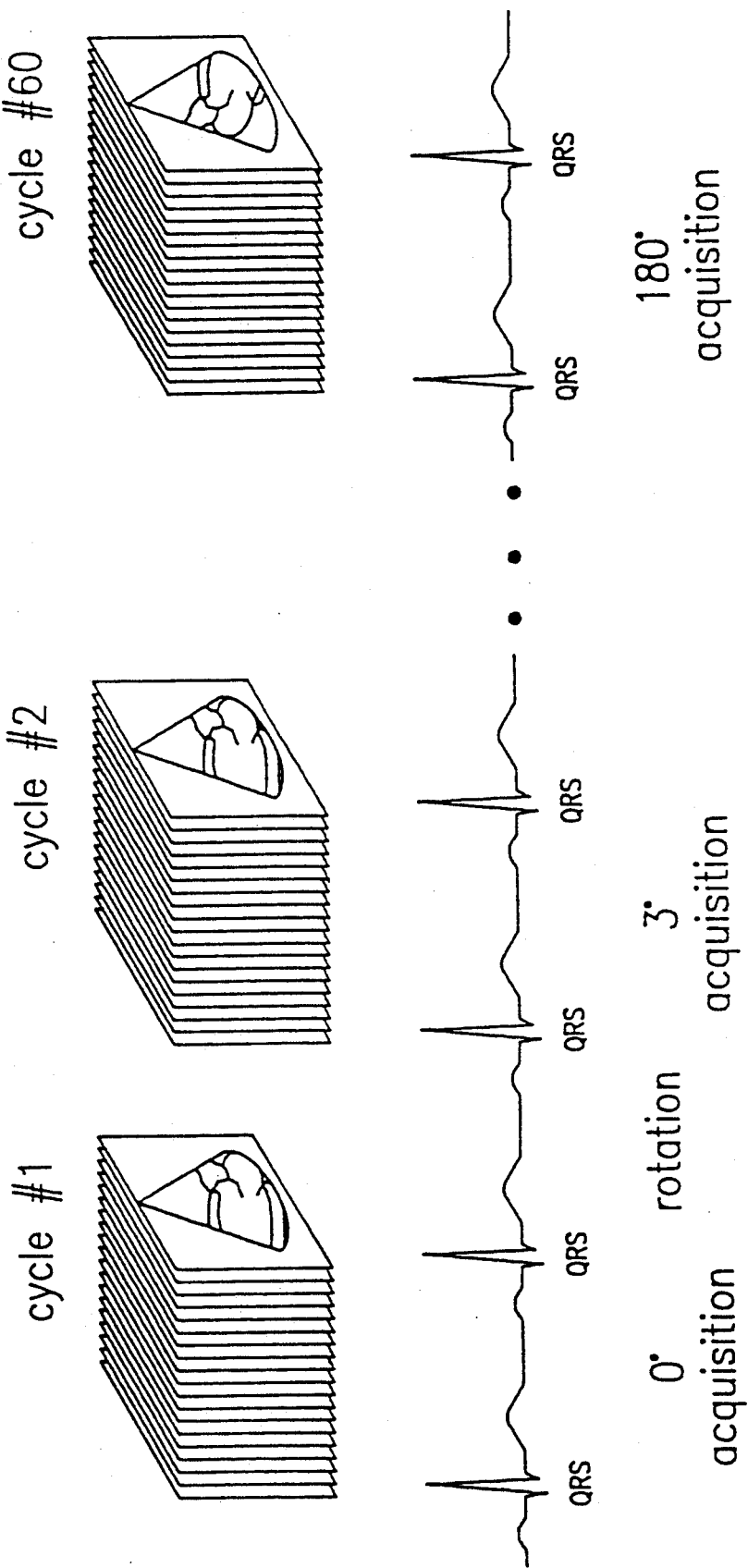
FIG. 8d shows a schematic representation of the acquisition process for the three-dimensional reconstruction of the heart throughout the entire cardiac cycle with the apparatus according to the present invention.

FIG. 8b shows the flow-chart of the program controlling the acquisition process of a system represented in FIG. 5 using a mechanical sector scanner transducer of the type shown in FIG. 2. The program is activated when the user pushes the START key on the function keyboard 218 (box 800). The program stops the sector scanning of the transducer (box 801) by sending a signal to the two-dimensional echographic system through the line 116. Thus, by means of the motor supply, the rotation controller 113 rotates the motor 14 to reset the transducer scanning plane in the starting position corresponding to 0 degrees rotation (box 802). If the user selected an ECG-gated acquisition (box 803), the program starts the execution of the ECG synchronism program described before (see FIG. 8a) (box 804); otherwise the program acquires immediately an image sending a signal to the two-dimensional echographic system 103 through the line 116 (box 805). The two-dimensional echographic system 103 acquires the images only when it receives the signal from the line 116; if this signal is zero, the system stops the acquisition at the end of a complete scanning to be sure that the piezoelectric ceramic is stopped anytime in the same position. Thus, if the program resets immediately the line 116 (box 806), the system acquires only a frame. After the acquisition of each image, the transducer is rotated (box 807) until a complete rotation of 180° is realized (box 808). If the user selected an ECG-gated acquisition, the program checks if a single frame or an entire cardiac cycle must be acquired (box 809). For a single frame acquisition, the program waits for the ECG synchronism signal (box 810) and, thus, it acquires a single image sending the start and stop signal to the two-dimensional echographic system 103 through the line 116 (boxes 811 and 812). When the next ECG synchronism is received (box 813), the program checks for the presence of an arrhythmia (box 814); if the rhythm is regular, the system rotates the transducer (box 815), otherwise it repeats the acquisition with the same transducer angular position. This acquisition process is repeated until a complete rotation of 180° is realized (box 816); then, the execution of the ECG synchronism program is stopped (box 817) and the process terminates. If the entire cardiac cycle acquisition is selected (box 819), the program waits for the ECG synchronism (box 818) and starts the acquisition of multiple images maintaining high the signal 116 sent to the two-dimensional echographic system 103 (box 819) until the next ECG synchronism is received (boxes 820 and 821). If the rhythm is irregular (box 822), the acquisition is repeated with the same transducer angular position; otherwise, the transducer angular position is incremented (box 823) and the process is repeated until a rotation of 180° is realized (box 824). When the acquisition is completed, the execution of the ECG synchronism program is stopped (box 817). Thus, if the user selects the ECG-gated acquisition of a single frame to reconstruct the heart in a specified moment of the cardiac cycle, the program branch ranging from box 810 to box 816 performs the acquisition of 60 images synchronized with the ECG as indicated in FIG. 8c. The program acquires an image every two cardiac cycles while, during the interposed cycles, the transducer is rotated in the next angular position. Therefore, to acquire the 60 images over an entire rotation of 180°, the system needs 120 cardiac cycles; the acquisition time is 72 to 120 seconds for a patient in sinus rhythm (heart rate ranging from 60 to 100 beats/second). The delay between the onset of the QRS and the acquisition time is selected by the digital switch on the function keyboard. If the user selects the ECG-gated acquisition of an entire cardiac cycle to reconstuct the heart during the entire cycle, the branch program ranging from box 818 to box 824 performs the acquisition of 60 cycles synchronized with the ECG as indicated in FIG. 8d. The system acquires an entire cardiac cycle starting from the onset of the QRS wave and ending with the onset of the next QRS wave; the time during the next cycle is used to rotate the transducer. As in FIG. 8c, this process is repeated 60 times for a total of 120 cardiac cycles.

As shown in FIG. 8e, the algorithm for the system presented in FIG. 6, using a probe like the one shown in FIG. 3, is similar to the flow-chart presented in FIG. 8b. The main difference is in the control of the acquisition/rotation sequence. In fact, with the transducer shown in FIG. 3, the program must drive the rotation/scanning selector and the motor (21) inside the probe to switch between the acquisition and the rotation status of the probe.

Figure 8F:
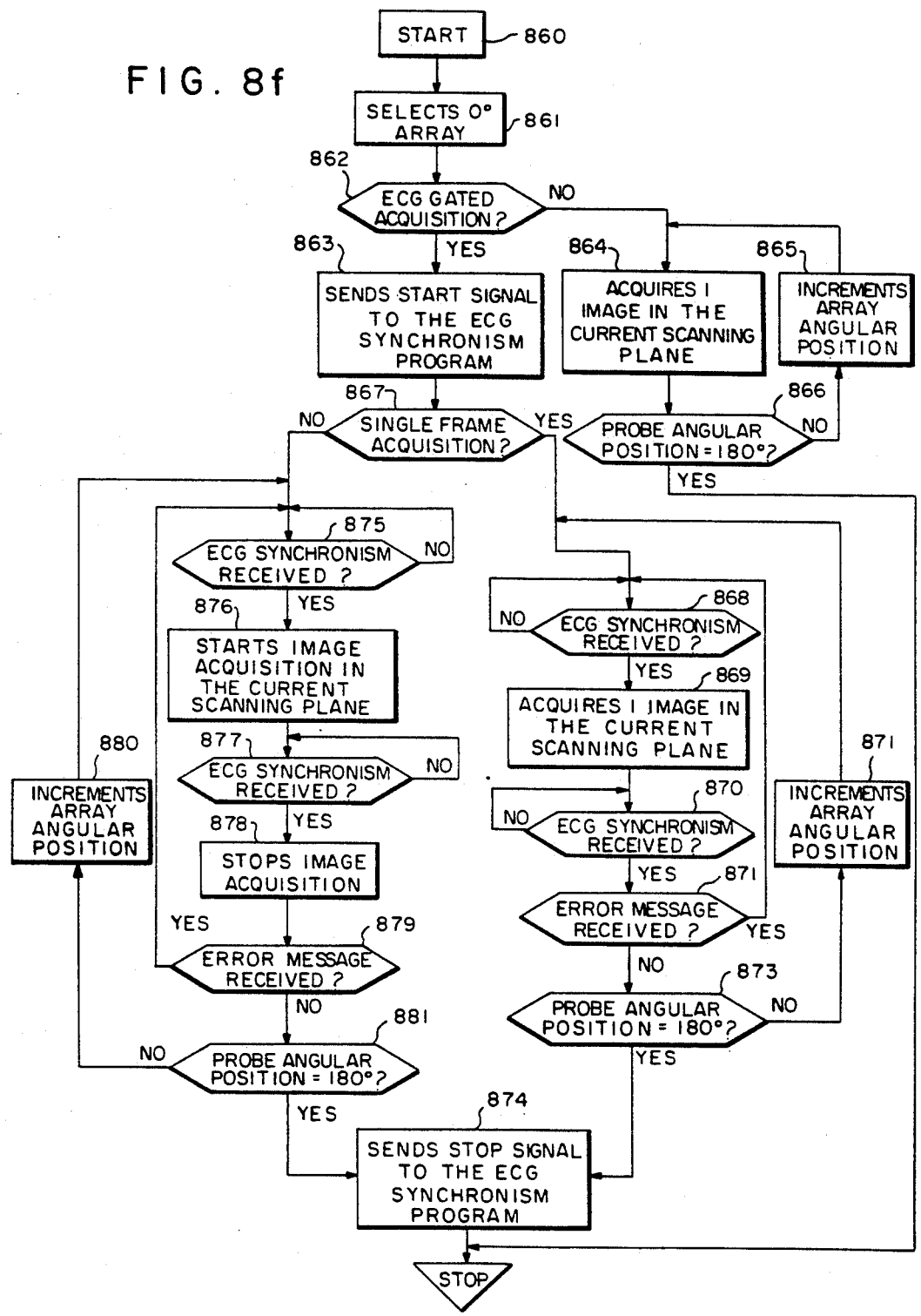
FIG. 8f shows a flow-chart of the program for acquiring a complete series of echographic images with the apparatus according to the present invention, provided with an electronic type of echographic sector-scan probe.

The system shown in FIG. 7 connected to an electronic transducer with a matrix of piezoelectric elements (FIG. 4) is controlled by the program shown in FIG. 8f. This flow-chart is similar to the FIG. 8b with the difference that the rotation of the scanning plane is realized selecting a different array of piezoelectric elements without any mechanical movement.

FIG. 8e shows the flow-chart of the program controlling the acquisition process of a system represented in FIG. 6 using a mechanical sector-scanner transducer of the type shown in FIG. 3. The program is activated when the user pushes the START key on the function keyboard 218 (box 830). The program interrupts the sectorial scanning of the transducer (box 831) by stopping the motor 21 when the transducer 33 is in the horizontal position. Thus, the rotation/scanning selector is switched in the rotation position (box 832) and the scanning plane is rotated to the starting position corresponding to 0° rotation (box 833). If the user selected an ECG-gated acquisition (box 834), the program starts the execution of the ECG synchronism program described before (see FIG. 8a) (box 835); otherwise the program switches the rotation/scanning selector in the scanning position (box 836) and acquires immediately an image driving the motor 21 that is connected with the transducer 33 (box 837). After the acquisition of each image, the rotation/scanning selector is switched in the rotation position (box 838) and the scanning plane is rotated (box 839) until a complete rotation of 180° is realized (box 840). If the user selected an ECG-gated acquisition, the program checks if a single frame or an entire cardiac cycle must be acquired (box 841). For a single frame acquisition, the program switches the rotation/scanning selector in the scanning position (box 842) and it waits for the ECG synchronism signal (box 843). When the ECG synchronism signal is received, the program acquires a single image driving the motor 21 connected with the transducer 33 (box 844). When the next ECG synchronism is received (box 845), the program checks for the presence of an arrhythmia (box 846); if the rhythm is regular, the system rotates the transducer switching the rotation/scanning selector to the rotation position (box 847) and incrementing the scanning plane angular position (box 848), otherwise it repeats the acquisition with the same transducer angular position. This acquisition process is repeated until a complete rotation of 180° is realized (box 849); then, the execution of the ECG synchronism program is stopped (box 850) and the process terminates. If the entire cardiac cycle acquisition is selected (box 841), the program switches the rotation/scanning selector to the scanning position (box 851) and it waits for the ECG syncrhonism (box 852). When the ECG synchronism is received, the program starts the acquisition of multiple images driving the motor 21 (box 853) until the next ECG synchronism is received (box 854). When the ECG synchronism indicates the end of the cardiac cycle, the program interrupts the image acquisition stopping the motor 21 connected with the transducer 33 (box 855). If the rhythm is irregular (box 856), the acquisition is repeated with the same transducer angular position; otherwise, the rotation/scanning selector is switched to the rotation position (box 857) and the transducer angular position is incremented (box 858). The acquisition/rotation sequence is repeated until a rotation of 180° is realized (box 859). When the acquisition is completed, the execution of the ECG synchronism program is stopped (box 850).

FIG. 8f shows the flow-chart of the program controlling the acquisition process of a system represented in FIG. 7 using an electronic sector-scanner transducer with a matrix of piezoelectric elements of the type shown in FIG. 4. The program is activated when the user pushes the START key on the function keyboard 265 (box 860). The program stops the sectorial scanning of the transducer and it selects the array of piezoelectric elements corresponding to 0° rotation (box 861). If the user selected an ECG-gated acquisition (box 862), the program starts the execution of the ECG synchronism program described before (see FIG. 8a) (box 863); otherwise the program acquires immediately an image on the current scanning plane (box 864). After the acquisition of each image, the scanning plane is rotated (box 865) and a new image is acquired until a complete rotation of 180° is realized (box 866). If the user selected an ECG-gated acquisition, the program checks if a single frame or an entire cardiac cycle must be acquired (box 867). For a single frame acquisition, the program waits for the ECG synchronism signal (box 868) When the ECG synchronism signal is received, the program acquires a single image (box 869). When the next ECG synchronism is received (box 870), the program checks for the presence of an arrhythmia (box 871); if the rhythm is regular, the system selects the next array of piezoelectric elements to rotate the scanning plane (box 872), otherwise it repeats the acquisition with the same transducer angular position. This acquisition process is repeated until a complete rotation of 180° is realized (box 873); then, the execution of the ECG synchronism program is stopped (box 874) and the process terminates. If the entire cardiac cycle acquisition is selected (box 867), the program waits for the ECG synchronism (box 875). When the ECG synchronism is received, the program starts the acquisition of multiple images (box 876) until the next ECG synchronism is received (box 854). When the ECG synchronism indicates the end of the cardiac cycle, the program stops the image acquisition (box 878). If the rhythm is irregular (box 879), the acquisition is repeated with the same transducer angular position; otherwise, the scanning plane is rotated selecting the next array of piezoelectric elements (box 880). The acquisition/rotation sequence is repeated until a rotation of 180° is realized (box 881). When the acquisition is completed, the execution of the ECG synchronism program is stopped (box 874).

Figure 9:
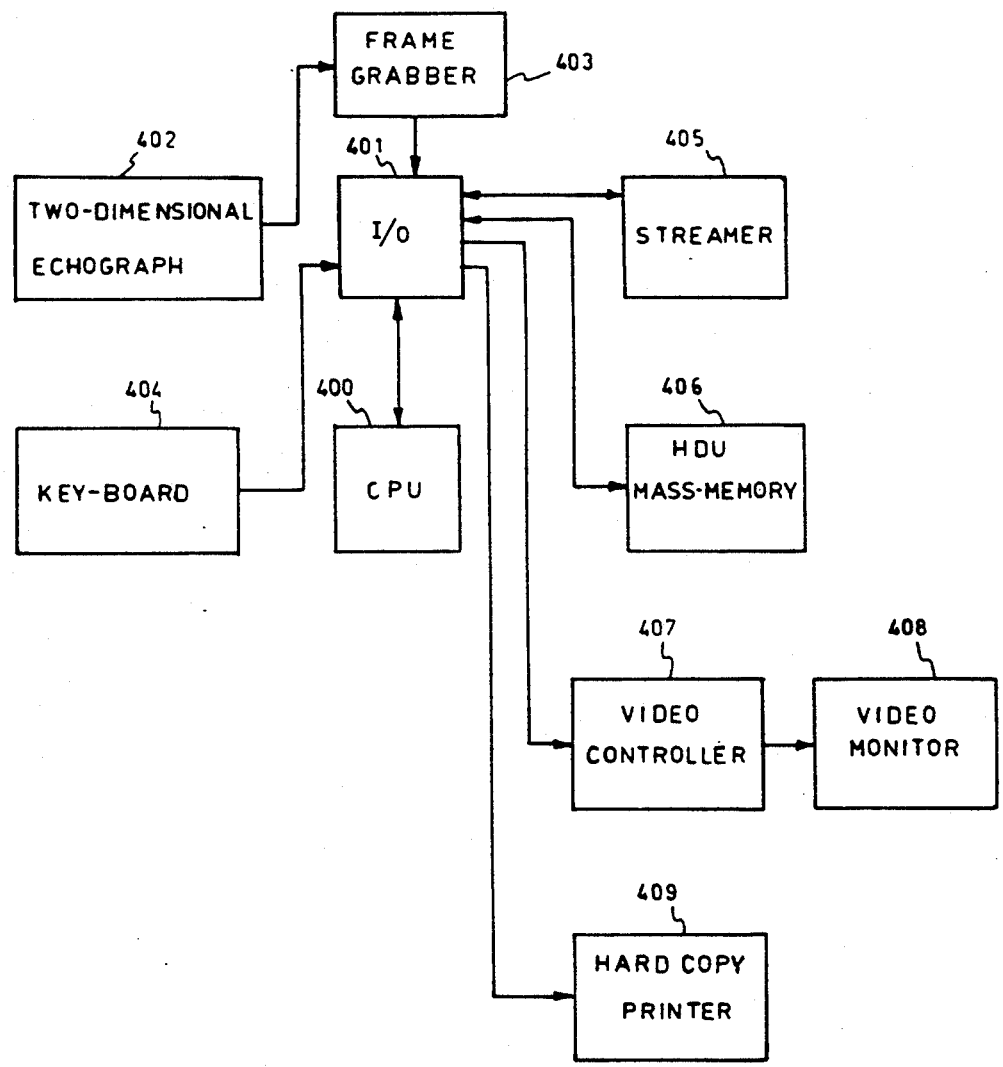
FIG. 9 shows a block diagram of the data processing apparatus and output devices of the apparatus according to the invention.

Reference will now be made to FIG. 9 showing the data processing arrangement for obtaining the three-dimensional reconstruction of echographic images from the data collected according to the apparatus and methods hereinbefore disclosed.

FIG. 9 shows a general purpose computing unit which could be realized either as a separate unit or incorporated in the processor-controlled units for obtaining two-dimensional echographic images.

As shown in FIG. 9, the data processing unit comprises a CPU 400 of a structure well known in the art, connected to an input/output unit 401. The input/output unit 401 is connected with:

a frame grabber 402 that digitizes the two-dimensional echographic images processed by the echographic unit 402;

a keyboard 404 to input various controls and commands to the apparatus;

a mass storage unit consisting of a magnetic tape streamer 405;

a Hard-Disk Unit mass memory apparatus 406;

a video controller 407 connected to a video monitor 408 either monochrome or color type; and, possibly, with a hard copy printer 409.

The CPU 400 operates under the control of software means either residing on a read only memory (not shown) or a random access memory, bootstrapped from a floppy disk unit (not shown).

Figure 10:
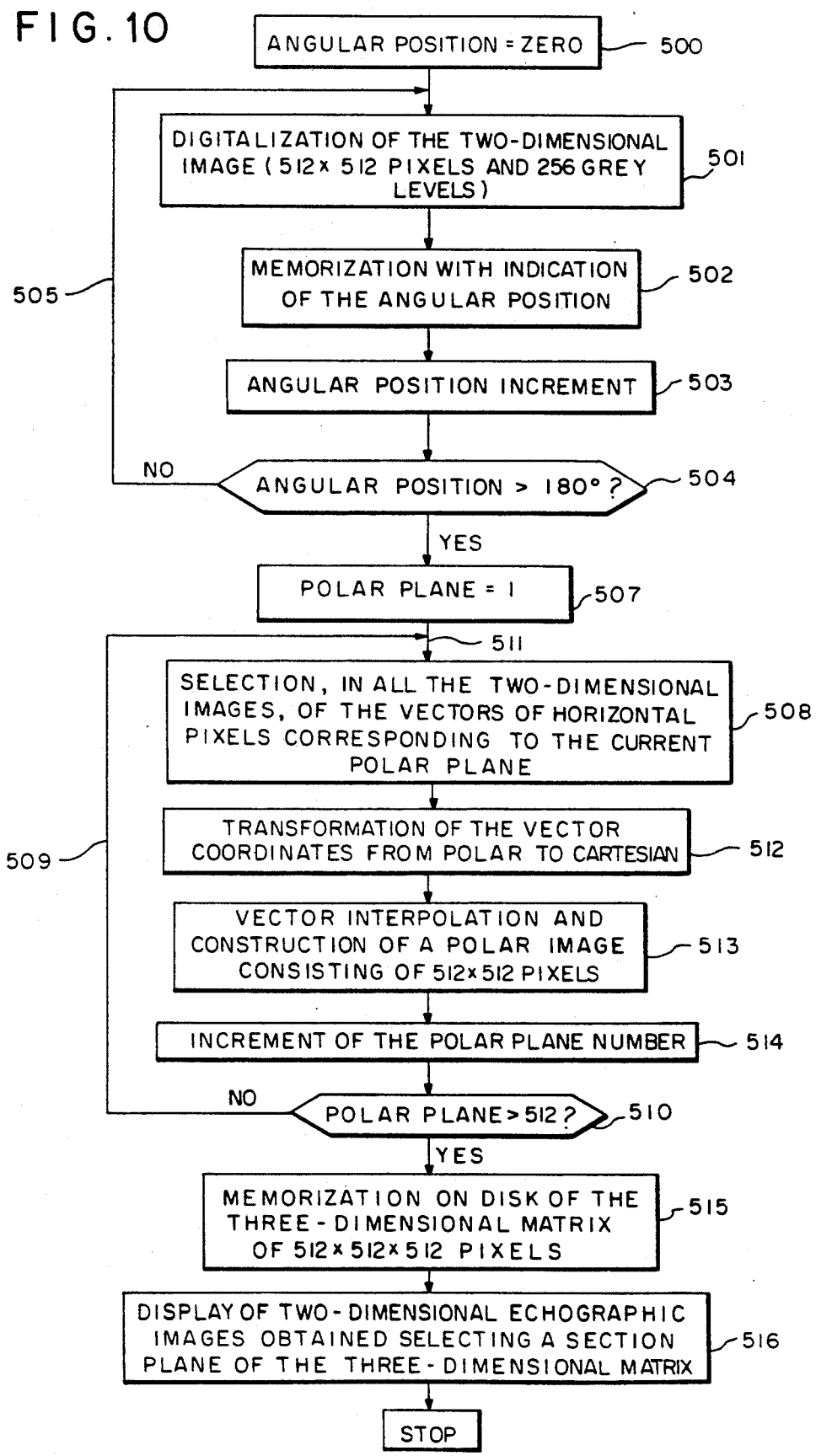
FIG. 10 shows a flow chart illustrating the general operation of the apparatus according to the present invention.

In FIG. 10 is shown a flow chart showing the operating program controlling the CPU 400 of FIG. 9.

The program shown in the flow-chart of FIG. 10 starts from box 500 at the statement that the rotating echographic scanning head is at its home position corresponding to the zero angular position.

At this point the digitization of a two-dimensional image is performed, for instance in a format of 512×512 pixels with 256 levels of grey (8 bits) (box 501). This image is memorized (box 502) for instance in a RAM memory with the insertion of additional information, e.g. the angular position of the scanning head (zero degrees in the first run of the loop).

Subsequently (box 503) the angular position of the scanning head is incremented through a predetermined angle, in a preferred embodiment through an angle of 3°. This process continues through 3° increment steps up to when the decision box 504 recognizes that the entire scanning of 180° has been performed. If the scanning is lower than 180° the loop repeats through line 505 which combines in 506 at the transition from box 500 to box 501.

At the YES output of decision box 504 a block of information is therefore available, comprising 180/3=60 two-dimensional images, labelled with their orientation angle as above explained (and possibly other information useful for the operator).

With box 507 a second processing step starts. Beginning with a polar plane equal to 1 (box 507) a selection is performed in box 508, in all the two-dimensional images, of the vectors corresponding to horizontal planes corresponding to the current polar plane identified by the loop returning on line 509 from decision box 510 to combination point 511.

The processing performed in box 508 is followed by a transformation of the vector coordinates from polar into cartesian ones (box 512). This is followed in box 513 by an interpolation of the above mentioned vector for the build-up of one polar image comprising 512×512 pixels. In box 514 an increment of the polar plane occurs, so that the operations of boxes 508, 512 and 513 are repeated until reaching a polar plane greater than 512, expressed by decision box 510.

At the end of this second processing step ranging from block 508 to block 510, a three-dimensional matrix with 512×512×512 pixels (128 M bytes) is available and ready to be stored on a hard disk unit (block 406 of FIG. 9) (box 515).

At this point, the display of two-dimensional tomographic images is possible, obtained by selecting a section plane of the three-dimensional matrix (box 516). This section will be displayed on a monitor, or a hard copy thereof may be made as previously described.

Figure 11:
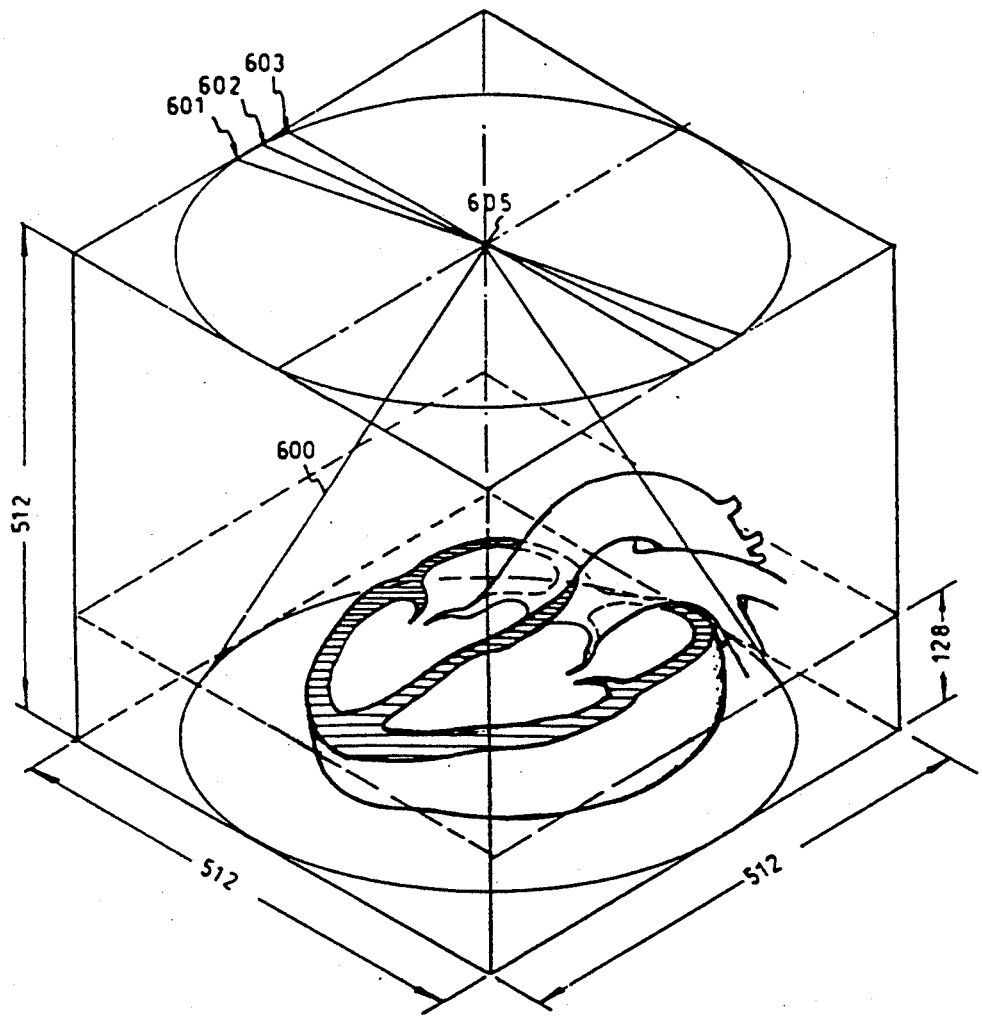
FIG. 11 shows a schematic representation of the three-dimensional matrix of information obtained with the process shown in FIG. 10.

The block of information which is built according to the invention is better shown in FIG. 11 as being constituted by a "cube" matrix having its sides 512 bytes long, wherein a "cone" 600 of information is enclosed, constituted by a number of scan planes 601, 602, 603 etc., corresponding to the single scan planes of the echographic probe before disclosed. The "cone" 600 has an apex 605 which corresponds to the tip of the probe lying against the body of a patient. Within the "cone" 600 is contained all the information representative of an anatomic structure schematized by a roughly represented heart 606.

With a software procedure as shown in the third part of the flow sheet diagram of FIG. 10 (block 516) a desired section may be obtained, for instance along the plane "128", thus obtaining a sectional view of the heart as shown in shadow in 607.

Of course, through data processing procedures well known in the art of processing of images, any other plane of section can be derived from the block of information schematically shown in FIG. 11. Section planes may be derived having different inclinations and orientation that have not been shown in FIG. 11 for the sake of clarity.

In fact, the "cone" 600 contains all the information about the anatomical structure, derived from the successive scans performed through an angle of 180° as previously described. When the algorithm described in FIG. 10 is applied to each frame of an entire cardiac cycle, a three-dimensional reconstruction of the heart in each moment of its cycle can be obtained.

The apparatus according to the invention, may also be used for the three-dimensional reconstruction of the blood flow utilizing a sector-scan probe color-coded for flow mapping by Doppler. The colour flow mapping two-dimensional Doppler echographic apparatus provide a two-dimensional image with superimposed a colour-coded map of the blood flows wherein the different colours encode different flow speeds and directions with respect to the transducer itself. This kind of representation allows the visualization of a section of the contour of the blood flow corresponding to the sectorial scanning plane, but does not provide any information about its actual extension and orientation in space. The acquisition of a plurality of two-dimensional images with a colour map of the blood flow, using a Doppler transducer according to the invention, allows the complete reconstruction of the three-dimensional contour of the blood flow under examination. Even with the transducer according to the invention, however, if the blood flow is exclusively perpendicular to the direction of the interrogating ultrasonic beam, it cannot be detected since the frequency shift produced by the Doppler effect is zero.

The apparatus according to the invention may be provided with an "invasive" probe, either flexible or rigid, of the rotating type with arrays of piezoelectric elements, or it can be provided with a probe of the fixed type having mounted on it a three-dimensional array of piezoelectric elements, so that it can be utilized, during invasive examinations, for the volumetric acquisition of signals produced by reflection and/or scattering from internal parts of anatomic structures.

It is to be remarked, finally, that the apparatus according to the present invention, besides the study of any organ of the human or animal body, may be conveniently used for non destructive tests in any other technical field.

Changes and/or modifications may be made in the apparatus according to the invention, without departing from the scope of the invention itself.

What is claimed is as follows:

1. An apparatus for obtaining three-dimensional echographic images comprising:
   a two-dimensional image scanning means having a piezoelectric transducer contained in an echographic probe, having means for movement in predetermined angular increments for a predetermined number of times;
   means for digitalization of each two-dimensional image produced by said two-dimensional image scanning means;
   means for recording each two-dimensional image and the angular position of the recorded image;
   means for selecting in all the two-dimensional images, the vectors of horizontal pixels corresponding to a current polar plane;
   means for transformation of said vector coordinates from polar to cartesian coordinates;
   means for vector interpolation and construction of a polar image consisting of pixels;
   means for incrementing the polar plane number;
   means for recording in memory the three-dimensional matrix of pixels; and
   means for display of two-dimensional echographic images obtained by selecting a section plane of the three-dimensional matrix.

2. The apparatus in accordance with claim 1, further comprising means for synchronizing acquisition of the two-dimensional image with an ECG-gated signal.

3. An apparatus for obtaining three dimensional echographic images of an anatomic structure from a series of successively produced two dimensional echographic images comprising
   an echographic probe having an ultrasound transducer contained as part of said probe;
   means to produce, according to a predetermined scanning plane, two dimensional echographic images through real-time processing of signals reflected and scattered by the anatomic structure when the structure is hit by a beam of ultrasound, connected to said ultrasound transducer;
   scanning control means connected to said probe, said means to produce two dimensional images including
   means for processing of received echographic signals and for the display of a two dimensional image from said signals;
   means for rotating the scanning plane, connected to said ultrasound transducer, wherein said ultrasound transducer produces said ultrasound beam through an overall angle by intermediate angular increments, having predetermined amplitude and frequency, around the longitudinal axis of said probe, while said probe remains stationary with respect to the anatomic structure;
   means for the actuation and control of a scanning sequence connected to said means for rotating the scanning plane;
   said ultrasound transducer having an axis orthogonal to the longitudinal axis of said probe;
   motor means connected to a rotatable support upon which said ultrasound transducer is mounted to transmit to said support angular displacements having a predetermined amplitude up to an overall rotation of 180 degrees;
   motion transmission means connected to said motor means to provide a rotating movement, having a predetermined amplitude along the scanning plane, around said axis of said transducer as a center of rotation;
   clutch means between said transmission means and said rotatable support for said probe for imparting to said rotatable support an angular displacement having the predetermined amplitude;
   means for control of said means to produce the two dimensional images, said means to provide rotating movement, and detection of the angular position of the said means to provide rotating movement.

4. An apparatus according to claim 3, wherein rotation control means are servoed to a rotation sensor and means are provided for indicating the instantaneous angular position of the transducer with respect to a reference position.

5. An apparatus according to claim 4, further comprising means for adding a numerical indication of said instantaneous angular position to the corresponding two-dimensional image, and means for adding being connected with said indicating means.

6. An apparatus according to claim 3, wherein said ultrasound transducer comprises a matrix of piezoelectric elements intersected orthogonally by said longitudinal axis of the probe in register with its center, and means for selecting electronically on said matrix single vectors constituted by a row of said elements, all passing through said center and rotating one with respect to the other through an angle having a predetermined amplitude, so as to individuate a reference scanning plane and a sequence of scanning planes in correspondence with each of said vectors, spaced through a known angle with respect to said reference scanning plane.

7. An apparatus according to claim 6 wherein said means for selecting electronically single vectors of piezoelectric elements on said matrix or arrays includes a multiplexer and programmable control means suitable for providing to the multiplexer the indication of which element to energize at each point in time.

8. An apparatus according to claim 3, wherein said ultrasound transducer comprises at least two arrays of piezoelectric elements crossing each other on the longitudinal axis of the probe in register with its center and means for selecting electronically single vectors by generating energizing and receiving delays of the single elements of each array, said vectors passing through said center and rotating one with respect to the other around said longitudinal axis through an angle having a predetermined amplitude, so as to individuate a reference scanning plane and a sequence of scanning planes in correspondence with each series of delays produced.

9. An apparatus according to claim 3 further comprising means for synchronizing electronically the rotation of the scanning plane with a physiological signal deriving from the anatomical structure being examined.

10. An apparatus according to claim 9, wherein said physiological signal is an electrocardiographic signal.

11. An apparatus according to claim 10 wherein said ultrasound transducer of said echographic probe includes piezoelectric sector-scan transducer elements for Doppler investigations.

12. An apparatus according to claim 11 wherein said means for processing of received echographic signals includes programmed computing means provided for constructing within a mass memory unit a three-dimensional block of information including all the information derived from a plurality of echographic scans taken successively of the structure being examined, said computing means being connected to program means for reconstructing two-dimensional sections of the examined structure under any desired plane or angle corresponding or different from the plane or angle under which each of said echographic scans has been initially made for constructing said three-dimensional block of information.

13. An apparatus according to claim 12, wherein each said echographic scan used for constructing said three-dimensional block of information is labelled with information relating to the angle of scan with respect to a reference angle.

14. An apparatus according to claim 13, wherein said computing means are associated to a control keyboard for selecting the parameters of a sectional image to be reconstructed from said three-dimensional block of information for the subsequent display on a video monitor.

15. An apparatus according to claim 14, wherein said computing means are connected to a hard copy unit for producing hard copy images of the video monitor display.

16. An apparatus according to claim 15 wherein Doppler transducer means included with said echographic probe for obtaining color-coded flow mapping information are provided for displaying additional information about Doppler shift caused by the flow of blood.

17. An apparatus according to claim 16, wherein said Doppler information is stored and displayed in colours different from the colour of structure information.

18. The apparatus according to claim 3 wherein
said ultrasound transducer is a piezoelectric transducer.

19. An apparatus according to claim 18, wherein said piezoelectric transducer is of the mechanical sector-scan type.

20. An apparatus according to claim 18, wherein said piezoelectric transducer is of the phased array sector-scan type.

21. The apparatus according to claim 3 wherein said clutch means is an electromagnetic clutch.

22. An apparatus according to claim 21, wherein said electromagnetic clutch includes an electromagnet fixed with respect to the housing of the probe, a male connection member integral with said motion transmission means and a female connection member, which is integral, with respect to rotation, with said rotatable support movable between an engagement position with said male member, when said electromagnet is de-energized, for connecting said motion transmission means to said rotatable support, and a rest position, in which it is spaced from said male member, in the condition of energized electromagnet, and elastic means suitable for operating on said female member against the action of said electromagnet.

23. The apparatus according to claim 3 wherein
said movement having a predetermined amplitude is an oscillating movement.

24. The apparatus according to claim 3 wherein said last mentioned means for control of a plurality of means is a microprocessor for programmed control.

25. An apparatus for obtaining three dimensional echographic images of an anatomic structure from a series of successively produced two dimensional echographic images comprising
an echographic probe having a transducer contained as part of said probe;
means to produce, according to a predetermined scanning lane, two dimensional echographic images through real-time processing of signals reflected and scattered by the anatomic structure when the structure is hit by a beam of ultrasound, connected to said transducer;
scanning control means connected to said probe,
said means to produce two dimensional images including
means for processing of received echographic signals and for the display of a two dimensional image from said signals;
means for rotating the scanning plane, connected to said transducer, wherein said transducer produces said ultrasound beam through an overall angle by intermediate angular increments, having predetermined amplitude and frequency, around the longitudinal axis of said probe, while said probe remains stationary with respect to the anatomic structure;

means for the actuation and control of a scanning sequence connected to said means for rotating the scanning plane;

and delay means for an electrocardiographic signal for starting acquisition of scans with presettable delays in order to record a three dimensional block of information in selected phases during a whole cardiac cycle.

26. An apparatus according to claim 25, wherein means are provided for suppressing unwanted electrocardiographic signals.

* * * * *